(12) United States Patent
Fife

(10) Patent No.: US 10,481,123 B2
(45) Date of Patent: *Nov. 19, 2019

(54) ION-SENSING CHARGE-ACCUMULATION CIRCUITS AND METHODS

(71) Applicant: LIFE TECHNOLOGIES CORPORATION, Carlsbad, CA (US)

(72) Inventor: Keith Fife, Palo Alto, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/789,850

(22) Filed: Oct. 20, 2017

(65) Prior Publication Data

US 2018/0202966 A1    Jul. 19, 2018

Related U.S. Application Data

(63) Continuation of application No. 14/964,938, filed on Dec. 10, 2015, now abandoned, which is a
(Continued)

(51) Int. Cl.
*G01N 27/414* (2006.01)
*G01N 27/30* (2006.01)

(52) U.S. Cl.
CPC ......... *G01N 27/414* (2013.01); *G01N 27/302* (2013.01); *G01N 27/4145* (2013.01); *G01N 27/4148* (2013.01)

(58) Field of Classification Search
CPC ............. G01N 27/414; G01N 27/4145; G01N 27/4148
(Continued)

(56) References Cited

U.S. PATENT DOCUMENTS

| 3,531,258 A | 9/1970 | Merrifield |
| 4,008,736 A | 2/1977 | Wittmann-Liebold et al. |

(Continued)

FOREIGN PATENT DOCUMENTS

| CN | 1582334 | 2/2005 |
| CN | 101676714 | 3/2010 |

(Continued)

OTHER PUBLICATIONS

"0V5640 Datasheet Product Specification", *1/4" color CMOS QSXGA (5 megapixel) image sensor with OmniBSI technology*, May 1, 2011, p. 1, line 9 and pp. 2-7, paragraph 1.
(Continued)

*Primary Examiner* — Bach T Dinh

(57) ABSTRACT

An ion-sensitive circuit can include a charge accumulation device, to accumulate a plurality of charge packets as a function of an ion concentration of a fluid, and at least one control and readout transistor, to generate an output signal as a function of the accumulated plurality of charge packets, the output signal representing the ion concentration of the solution. The charge accumulation device can include a first charge control electrode above a first electrode semiconductor region, an electrically floating gate structure above a gate semiconductor region and below an ion-sensitive passivation surface, a second charge control electrode above a second electrode semiconductor region, and a drain diffusion region. The first control electrode can control entry of charge into a gate semiconductor region in response to a first control signal. The ion-sensitive passivation surface can be configured to receive the fluid. The second charge control electrode can control transmission of the plurality of charge packets out of the gate semiconductor region and into the drain diffusion region in response to a second control signal. The drain diffusion region can receive the plurality of charge
(Continued)

packets from the gate semiconductor region via the second electrode semiconductor region.

4 Claims, 7 Drawing Sheets

Related U.S. Application Data continuation of application No. 14/477,125, filed on Sep. 4, 2014, now Pat. No. 9,239,313, which is a continuation of application No. 13/173,146, filed on Jun. 30, 2011, now Pat. No. 8,858,782.

(60) Provisional application No. 61/361,403, filed on Jul. 3, 2010, provisional application No. 61/360,495, filed on Jul. 1, 2010, provisional application No. 61/360,493, filed on Jun. 30, 2010.

(58) Field of Classification Search
USPC .............................................. 205/793.5, 792
See application file for complete search history.

(56) References Cited

U.S. PATENT DOCUMENTS

| | | |
|---|---|---|
| 4,086,642 A | 4/1978 | Yoshida et al. |
| 4,133,735 A | 1/1979 | Afromowitz et al. |
| 4,411,741 A | 10/1983 | Janata |
| 4,437,969 A | 3/1984 | Covington et al. |
| 4,438,354 A | 3/1984 | Haque et al. |
| 4,444,644 A | 4/1984 | Hiramoto |
| 4,490,678 A | 12/1984 | Kuisl et al. |
| 4,558,845 A | 12/1985 | Hunkapiller |
| 4,641,084 A | 2/1987 | Komatsu |
| 4,660,063 A | 4/1987 | Anthony |
| 4,691,167 A | 9/1987 | Vlekkert et al. |
| 4,701,253 A | 10/1987 | Ligtenberg et al. |
| 4,722,830 A | 2/1988 | Urie et al. |
| 4,743,954 A | 5/1988 | Brown |
| 4,764,797 A | 8/1988 | Shaw et al. |
| 4,777,019 A | 10/1988 | Dandekar |
| 4,822,566 A | 4/1989 | Newman |
| 4,863,849 A | 9/1989 | Melamede |
| 4,864,229 A | 9/1989 | Lauks et al. |
| 4,874,499 A | 10/1989 | Smith et al. |
| 4,893,088 A | 1/1990 | Myers et al. |
| 4,927,736 A | 5/1990 | Mueller et al. |
| 4,971,903 A | 11/1990 | Hyman |
| 5,009,766 A | 4/1991 | Lauks |
| 5,038,192 A | 8/1991 | Bonneau |
| 5,082,788 A | 1/1992 | Farnsworth et al. |
| 5,110,441 A | 5/1992 | Kinlen et al. |
| 5,113,870 A | 5/1992 | Rossenfeld |
| 5,118,607 A | 6/1992 | Bignami et al. |
| 5,126,022 A | 6/1992 | Soane et al. |
| 5,126,759 A | 6/1992 | Small et al. |
| 5,132,418 A | 7/1992 | Caruthers et al. |
| 5,138,251 A | 8/1992 | Koshiishi et al. |
| 5,140,393 A | 8/1992 | Hijikihigawa et al. |
| 5,142,236 A | 8/1992 | Maloberti et al. |
| 5,151,587 A | 9/1992 | Machida et al. |
| 5,151,759 A | 9/1992 | Vinal |
| 5,164,319 A | 11/1992 | Hafeman et al. |
| 5,202,576 A | 4/1993 | David et al. |
| 5,284,566 A | 2/1994 | Cuomo et al. |
| 5,313,984 A | 5/1994 | Garwood, Jr. et al. |
| 5,317,407 A | 5/1994 | Michon |
| 5,319,226 A | 6/1994 | Sohn et al. |
| 5,407,854 A | 4/1995 | Baxter et al. |
| 5,436,149 A | 7/1995 | Barnes |
| 5,439,839 A | 8/1995 | Jang |
| 5,466,348 A | 11/1995 | Holm-Kennedy |
| 5,475,337 A | 12/1995 | Tatsumi |
| 5,490,971 A | 2/1996 | Gifford et al. |
| 5,498,392 A | 3/1996 | Wilding et al. |
| 5,520,787 A | 5/1996 | Hanagan et al. |
| 5,554,339 A | 9/1996 | Cozzette et al. |
| 5,583,462 A | 12/1996 | Grasshoff |
| 5,587,128 A | 12/1996 | Wilding et al. |
| 5,587,894 A | 12/1996 | Naruo |
| 5,593,838 A | 1/1997 | Zanzucchi et al. |
| 5,600,451 A | 2/1997 | Maki |
| 5,627,403 A | 5/1997 | Bacchetta et al. |
| 5,631,704 A | 5/1997 | Dickinson et al. |
| 5,637,469 A | 6/1997 | Wilding et al. |
| 5,646,558 A | 7/1997 | Jamshidi et al. |
| 5,650,649 A | 7/1997 | Tsukiji |
| 5,702,964 A | 12/1997 | Lee |
| 5,793,230 A | 8/1998 | Chu et al. |
| 5,830,645 A | 11/1998 | Pinkel et al. |
| 5,846,708 A | 12/1998 | Hollis et al. |
| 5,894,284 A | 4/1999 | Garrity et al. |
| 5,907,765 A | 5/1999 | Lescouzeres et al. |
| 5,911,873 A | 6/1999 | McCarron et al. |
| 5,912,560 A | 6/1999 | Pasternak |
| 5,922,591 A | 7/1999 | Anderson et al. |
| 5,923,421 A | 7/1999 | Rajic et al. |
| 5,944,970 A | 8/1999 | Rosenblatt |
| 5,958,703 A | 9/1999 | Dower et al. |
| 5,965,452 A | 10/1999 | Kovacs |
| 6,001,299 A | 12/1999 | Kawabe et al. |
| 6,002,299 A | 12/1999 | Thomsen |
| 6,010,607 A | 1/2000 | Ramsey |
| 6,021,172 A | 2/2000 | Fossum et al. |
| 6,033,546 A | 3/2000 | Ramsey |
| 6,054,034 A | 4/2000 | Soane et al. |
| 6,107,032 A | 8/2000 | Kilger et al. |
| 6,191,444 B1 | 2/2001 | Clampitt et al. |
| 6,195,585 B1 | 2/2001 | Karunasiri et al. |
| 6,210,891 B1 | 4/2001 | Nyren et al. |
| 6,255,678 B1 | 7/2001 | Sawada et al. |
| 6,262,568 B1 | 7/2001 | Komatsu et al. |
| 6,274,320 B1 | 8/2001 | Rothberg et al. |
| 6,275,061 B1 | 8/2001 | Tomita |
| 6,280,586 B1 | 8/2001 | Wolf et al. |
| 6,294,133 B1 | 9/2001 | Sawada et al. |
| 6,327,410 B1 | 12/2001 | Walt et al. |
| 6,353,324 B1 | 3/2002 | Uber, III et al. |
| 6,355,431 B1 | 3/2002 | Chee et al. |
| 6,361,671 B1 | 3/2002 | Mathies et al. |
| 6,372,291 B1 | 4/2002 | Hua et al. |
| 6,376,256 B1 | 4/2002 | Dunnington et al. |
| 6,384,684 B1 | 5/2002 | Redman-White |
| 6,399,952 B1 | 6/2002 | Maher et al. |
| 6,403,957 B1 | 6/2002 | Fodor et al. |
| 6,406,848 B1 | 6/2002 | Bridgham et al. |
| 6,413,792 B1 | 7/2002 | Sauer et al. |
| 6,429,027 B1 | 8/2002 | Chee et al. |
| 6,432,360 B1 | 8/2002 | Church |
| 6,433,386 B1 | 8/2002 | Yun et al. |
| 6,459,398 B1 | 10/2002 | Gureshnik et al. |
| 6,465,178 B2 | 10/2002 | Chappa et al. |
| 6,475,728 B1 | 11/2002 | Martin et al. |
| 6,482,639 B2 | 11/2002 | Snow et al. |
| 6,485,944 B1 | 11/2002 | Church et al. |
| 6,490,220 B1 | 12/2002 | Merritt et al. |
| 6,499,499 B2 | 12/2002 | Dantsker et al. |
| 6,511,803 B1 | 1/2003 | Church et al. |
| 6,518,024 B2 | 2/2003 | Choong et al. |
| 6,518,146 B1 | 2/2003 | Singh et al. |
| 6,535,824 B1 | 3/2003 | Mansky et al. |
| 6,537,881 B1 | 3/2003 | Rangarajan et al. |
| 6,538,593 B2 | 3/2003 | Yang et al. |
| 6,545,620 B2 | 4/2003 | Groeneweg |
| 6,571,189 B2 | 5/2003 | Jensen et al. |
| 6,602,702 B1 | 8/2003 | McDevitt et al. |
| 6,605,428 B2 | 8/2003 | Kilger et al. |
| 6,613,513 B1 | 9/2003 | Parce et al. |
| 6,613,525 B2 | 9/2003 | Nelson et al. |
| 6,618,083 B1 | 9/2003 | Chen et al. |
| 6,624,637 B1 | 9/2003 | Pechstein |
| 6,627,154 B1 | 9/2003 | Goodman et al. |
| 6,654,505 B2 | 11/2003 | Bridgham et al. |

(56) References Cited

U.S. PATENT DOCUMENTS

| | | |
|---|---|---|
| 6,657,269 B2 | 12/2003 | Migliorato et al. |
| 6,671,341 B1 | 12/2003 | Kinget et al. |
| 6,682,899 B2 | 1/2004 | Bryan et al. |
| 6,682,936 B2 | 1/2004 | Kovacs |
| 6,686,638 B2 | 2/2004 | Fischer et al. |
| 6,700,814 B1 | 3/2004 | Nahas et al. |
| 6,703,660 B2 | 3/2004 | Yitzchaik et al. |
| 6,716,629 B2 | 4/2004 | Hess et al. |
| 6,762,022 B2 | 7/2004 | Makarov et al. |
| 6,770,472 B2 | 8/2004 | Manalis et al. |
| 6,780,591 B2 | 8/2004 | Williams et al. |
| 6,787,111 B2 | 9/2004 | Roach et al. |
| 6,795,006 B1 | 9/2004 | Delight et al. |
| 6,806,052 B2 | 10/2004 | Bridgham et al. |
| 6,828,100 B1 | 12/2004 | Ronaghi |
| 6,831,994 B2 | 12/2004 | Bridgham et al. |
| 6,841,128 B2 | 1/2005 | Kambara et al. |
| 6,859,570 B2 | 2/2005 | Walt et al. |
| 6,878,255 B1 | 4/2005 | Wang et al. |
| 6,888,194 B2 | 5/2005 | Yoshino |
| 6,898,121 B2 | 5/2005 | Chien et al. |
| 6,906,524 B2 | 6/2005 | Chung et al. |
| 6,919,211 B1 | 7/2005 | Fodor et al. |
| 6,926,865 B2 | 8/2005 | Howard |
| 6,927,045 B2 | 8/2005 | Hadd et al. |
| 6,929,944 B2 | 8/2005 | Matson |
| 6,939,451 B2 | 9/2005 | Zhao et al. |
| 6,953,958 B2 | 10/2005 | Baxter et al. |
| 6,958,216 B2 | 10/2005 | Kelley et al. |
| 6,960,437 B2 | 11/2005 | Enzelberger et al. |
| 6,969,488 B2 | 11/2005 | Bridgham et al. |
| 6,998,274 B2 | 2/2006 | Chee et al. |
| 7,008,550 B2 | 3/2006 | Li et al. |
| 7,019,305 B2 | 3/2006 | Eversmann et al. |
| 7,022,288 B1 | 4/2006 | Boss |
| 7,033,754 B2 | 4/2006 | Chee et al. |
| 7,037,687 B2 | 5/2006 | Williams et al. |
| 7,045,097 B2 | 5/2006 | Kovacs |
| 7,049,645 B2 | 5/2006 | Sawada et al. |
| 7,060,431 B2 | 6/2006 | Chee et al. |
| 7,067,886 B2 | 6/2006 | Bonges et al. |
| 7,084,641 B2 | 8/2006 | Brederlow et al. |
| 7,085,502 B2 | 8/2006 | Shushakob et al. |
| 7,087,387 B2 | 8/2006 | Gerdes et al. |
| 7,090,975 B2 | 8/2006 | Shultz et al. |
| 7,091,059 B2 | 8/2006 | Rhodes |
| 7,092,757 B2 | 8/2006 | Larson et al. |
| 7,097,973 B1 | 8/2006 | Zenhausern |
| 7,105,300 B2 | 9/2006 | Parce et al. |
| 7,106,089 B2 | 9/2006 | Nakano et al. |
| 7,129,554 B2 | 10/2006 | Lieber et al. |
| 7,169,560 B2 | 1/2007 | Lapidus et al. |
| 7,173,445 B2 | 2/2007 | Fujii et al. |
| 7,190,026 B2 | 3/2007 | Lotfi et al. |
| 7,192,745 B2 | 3/2007 | Jaeger |
| 7,193,453 B2 | 3/2007 | Wei et al. |
| 7,211,390 B2 | 5/2007 | Rothberg |
| 7,220,550 B2 | 5/2007 | Keen |
| 7,223,371 B2 | 5/2007 | Hayenga et al. |
| 7,223,540 B2 | 5/2007 | Pourmand et al. |
| 7,226,734 B2 | 6/2007 | Chee et al. |
| 7,229,799 B2 | 6/2007 | Williams |
| 7,235,389 B2 | 6/2007 | Lim et al. |
| 7,238,323 B2 | 7/2007 | Knapp et al. |
| 7,239,188 B1 | 7/2007 | Xu et al. |
| 7,244,559 B2 | 7/2007 | Rothberg et al. |
| 7,244,567 B2 | 7/2007 | Chen et al. |
| 7,264,929 B2 | 9/2007 | Rothberg et al. |
| 7,264,934 B2 | 9/2007 | Fuller |
| 7,265,929 B2 | 9/2007 | Umeda et al. |
| 7,267,751 B2 | 9/2007 | Gelbart et al. |
| 7,276,749 B2 | 10/2007 | Martin et al. |
| 7,279,588 B2 | 10/2007 | Hong et al. |
| 7,282,370 B2 | 10/2007 | Bridgham et al. |
| 7,285,384 B2 | 10/2007 | Fan et al. |
| 7,291,496 B2 | 11/2007 | Holm-Kennedy |
| 7,297,518 B2 | 11/2007 | Quake et al. |
| 7,298,475 B2 | 11/2007 | Gandhi et al. |
| 7,303,875 B1 | 12/2007 | Bock et al. |
| 7,317,216 B2 | 1/2008 | Holm-Kennedy |
| 7,317,484 B2 | 1/2008 | Dosluoglu et al. |
| 7,323,305 B2 | 1/2008 | Leamon et al. |
| 7,335,526 B2 | 2/2008 | Peters et al. |
| 7,335,762 B2 | 2/2008 | Rothberg et al. |
| 7,359,058 B2 | 4/2008 | Kranz et al. |
| 7,361,946 B2 | 4/2008 | Johnson et al. |
| 7,363,717 B2 | 4/2008 | Ekseth et al. |
| 7,381,936 B2 | 6/2008 | Tan et al. |
| 7,394,263 B2 | 7/2008 | Pechstein et al. |
| 7,419,636 B2 | 9/2008 | Aker et al. |
| 7,425,431 B2 | 9/2008 | Church et al. |
| 7,455,971 B2 | 11/2008 | Chee et al. |
| 7,462,452 B2 | 12/2008 | Williams et al. |
| 7,462,512 B2 | 12/2008 | Levon et al. |
| 7,462,709 B2 | 12/2008 | Jaeger |
| 7,465,512 B2 | 12/2008 | Wright et al. |
| 7,466,258 B1 | 12/2008 | Akopyan et al. |
| 7,470,352 B2 | 12/2008 | Eversmann et al. |
| 7,476,504 B2 | 1/2009 | Turner |
| 7,482,153 B2 | 1/2009 | Okada et al. |
| 7,482,677 B2 | 1/2009 | Lee et al. |
| 7,499,513 B1 | 3/2009 | Tetzlaff et al. |
| 7,515,124 B2 | 4/2009 | Yaguma et al. |
| 7,534,097 B2 | 5/2009 | Wong et al. |
| 7,538,827 B2 | 5/2009 | Chou |
| 7,575,865 B2 | 8/2009 | Leamon et al. |
| 7,576,037 B2 | 8/2009 | Engelhardt et al. |
| 7,590,211 B1 | 9/2009 | Burney |
| 7,595,883 B1 | 9/2009 | El Gamal et al. |
| 7,605,650 B2 | 10/2009 | Forbes |
| 7,608,810 B2 | 10/2009 | Yamada |
| 7,609,093 B2 | 10/2009 | Sarig et al. |
| 7,609,303 B1 | 10/2009 | Lee |
| 7,612,369 B2 | 11/2009 | Stasiak |
| 7,612,817 B2 | 11/2009 | Tay |
| 7,614,135 B2 | 11/2009 | Santini, Jr. et al. |
| 7,622,294 B2 | 11/2009 | Walt et al. |
| 7,645,596 B2 | 1/2010 | Williams et al. |
| 7,649,358 B2 | 1/2010 | Toumazou et al. |
| 7,667,501 B2 | 2/2010 | Surendranath et al. |
| 7,686,929 B2 | 3/2010 | Toumazou et al. |
| 7,695,907 B2 | 4/2010 | Miyahara et al. |
| 7,733,401 B2 | 6/2010 | Takeda |
| 7,772,383 B2 | 8/2010 | Chakrabarti et al. |
| 7,785,785 B2 | 8/2010 | Pourmand et al. |
| 7,785,790 B1 | 8/2010 | Church et al. |
| 7,794,584 B2 | 9/2010 | Chodavarapu et al. |
| 7,821,806 B2 | 10/2010 | Horiuchi |
| 7,824,900 B2 | 11/2010 | Iwadate et al. |
| 7,838,226 B2 | 11/2010 | Kamahori et al. |
| 7,842,377 B2 | 11/2010 | Lanphere et al. |
| 7,842,457 B2 | 11/2010 | Berka et al. |
| 7,859,029 B2 | 12/2010 | Lee et al. |
| 7,859,291 B2 | 12/2010 | Kim |
| 7,875,440 B2 | 1/2011 | Williams et al. |
| 7,884,398 B2 | 2/2011 | Levon et al. |
| 7,885,490 B2 | 2/2011 | Heideman et al. |
| 7,888,013 B2 | 2/2011 | Miyahara et al. |
| 7,888,015 B2 | 2/2011 | Toumazou et al. |
| 7,888,708 B2 | 2/2011 | Yazawa et al. |
| 7,890,891 B2 | 2/2011 | Stuber et al. |
| 7,898,277 B2 | 3/2011 | Weir |
| 7,923,240 B2 | 4/2011 | Su |
| 7,927,797 B2 | 4/2011 | Nobile et al. |
| 7,932,034 B2 | 4/2011 | Esfandyarpour et al. |
| 7,948,015 B2 | 5/2011 | Rothberg et al. |
| 7,955,995 B2 | 6/2011 | Kakehata et al. |
| 7,960,776 B2 | 6/2011 | Kim et al. |
| 7,972,828 B2 | 7/2011 | Ward et al. |
| 7,981,362 B2 | 7/2011 | Glezer et al. |
| 8,012,690 B2 | 9/2011 | Berka et al. |
| 8,017,938 B2 | 9/2011 | Gomez et al. |
| 8,035,175 B2 | 10/2011 | Shim et al. |
| 8,052,863 B2 | 11/2011 | Suzuki et al. |

(56) References Cited

U.S. PATENT DOCUMENTS

| | | |
|---|---|---|
| 8,067,731 B2 | 11/2011 | Matyjaszczyk et al. |
| 8,072,188 B2 | 12/2011 | Yorinobu et al. |
| 8,114,591 B2 | 2/2012 | Toumazou et al. |
| 8,124,936 B1 | 2/2012 | Lagna |
| 8,133,698 B2 | 3/2012 | Silver |
| 8,138,496 B2 | 3/2012 | Li et al. |
| 8,154,480 B2 | 4/2012 | Shishido et al. |
| 8,199,859 B2 | 6/2012 | Zerbe et al. |
| 8,217,433 B1 | 7/2012 | Fife |
| 8,227,877 B2 | 7/2012 | Lee et al. |
| 8,231,831 B2 | 7/2012 | Hartzell et al. |
| 8,232,813 B2 | 7/2012 | Burdett et al. |
| 8,247,849 B2 | 8/2012 | Fife et al. |
| 8,248,356 B2 | 8/2012 | Chen |
| 8,262,900 B2 | 9/2012 | Rothberg et al. |
| 8,263,336 B2 | 9/2012 | Rothberg et al. |
| 8,264,014 B2 | 9/2012 | Rothberg et al. |
| 8,269,261 B2 | 9/2012 | Rothberg |
| 8,277,628 B2 | 10/2012 | Ronaghi et al. |
| 8,293,082 B2 | 10/2012 | Rothberg et al. |
| 8,306,757 B2 | 11/2012 | Rothberg et al. |
| 8,313,625 B2 | 11/2012 | Rothberg et al. |
| 8,313,639 B2 | 11/2012 | Rothberg et al. |
| 8,317,999 B2 | 11/2012 | Rothberg et al. |
| 8,340,914 B2 | 12/2012 | Gatewood et al. |
| 8,343,856 B2 | 1/2013 | Therrien et al. |
| 8,349,167 B2 | 1/2013 | Rothberg et al. |
| 8,357,547 B2 | 1/2013 | Lee et al. |
| 8,361,713 B2 | 1/2013 | Bridgham et al. |
| 8,383,396 B2 | 2/2013 | Kamahori et al. |
| 8,415,716 B2 | 4/2013 | Rothberg et al. |
| 8,421,437 B2 | 4/2013 | Levine |
| 8,426,898 B2 | 4/2013 | Rothberg et al. |
| 8,426,899 B2 | 4/2013 | Rothberg et al. |
| 8,435,395 B2 | 5/2013 | Rothberg et al. |
| 8,441,044 B2 | 5/2013 | Rothberg et al. |
| 8,445,194 B2 | 5/2013 | Drmanac et al. |
| 8,445,945 B2 | 5/2013 | Rothberg et al. |
| 8,449,824 B2 | 5/2013 | Sun |
| 8,450,781 B2 | 5/2013 | Rothberg et al. |
| 8,470,164 B2 | 6/2013 | Rothberg et al. |
| 8,487,790 B2 | 7/2013 | Fife et al. |
| 8,492,800 B2 | 7/2013 | Rothberg et al. |
| 8,496,802 B2 | 7/2013 | Rothberg et al. |
| 8,502,278 B2 | 8/2013 | Rothberg et al. |
| 8,519,448 B2 | 8/2013 | Rothberg et al. |
| 8,524,057 B2 | 9/2013 | Rothberg et al. |
| 8,530,941 B2 | 9/2013 | Rothberg et al. |
| 8,535,513 B2 | 9/2013 | Rothberg et al. |
| 8,552,771 B1 | 10/2013 | Jordan et al. |
| 8,558,288 B2 | 10/2013 | Rothberg et al. |
| 8,575,664 B2 | 11/2013 | Rothberg et al. |
| 8,592,154 B2 | 11/2013 | Rearick |
| 8,653,567 B2 | 2/2014 | Fife |
| 8,658,017 B2 | 2/2014 | Rothberg et al. |
| 8,673,627 B2 | 3/2014 | Nobile et al. |
| 8,685,230 B2 | 4/2014 | Rothberg et al. |
| 8,685,298 B2 | 4/2014 | Rothberg et al. |
| 8,728,844 B1 | 5/2014 | Liu et al. |
| 8,731,847 B2 | 5/2014 | Johnson et al. |
| 8,742,469 B2 | 6/2014 | Milgrew |
| 8,742,472 B2 | 6/2014 | Rothberg et al. |
| 8,747,748 B2 | 6/2014 | Li et al. |
| 8,748,947 B2 | 6/2014 | Milgrew et al. |
| 8,764,969 B2 | 7/2014 | Rothberg et al. |
| 8,766,327 B2 | 7/2014 | Milgrew |
| 8,766,328 B2 | 7/2014 | Rothberg et al. |
| 8,776,573 B2 | 7/2014 | Rearick et al. |
| 8,786,331 B2 | 7/2014 | Jordan et al. |
| 8,796,036 B2 | 8/2014 | Fife et al. |
| 8,821,798 B2 | 9/2014 | Bustillo et al. |
| 8,823,380 B2 | 9/2014 | Levine et al. |
| 8,841,217 B1 | 9/2014 | Fife et al. |
| 8,847,637 B1 | 9/2014 | Guyton |
| 8,858,782 B2 * | 10/2014 | Fife .................. G01N 27/4148 205/793.5 |
| 8,912,005 B1 | 12/2014 | Fife et al. |
| 8,936,763 B2 | 1/2015 | Rothberg et al. |
| 8,945,912 B2 | 2/2015 | Bashir et al. |
| 8,962,366 B2 | 2/2015 | Putnam et al. |
| 8,963,216 B2 | 2/2015 | Fife et al. |
| 8,983,783 B2 | 3/2015 | Johnson et al. |
| 9,023,674 B2 | 5/2015 | Shen et al. |
| 9,164,070 B2 | 10/2015 | Fife |
| 9,201,041 B2 | 12/2015 | Dalton et al. |
| 9,239,313 B2 | 1/2016 | Fife |
| 9,270,264 B2 | 2/2016 | Jordan et al. |
| 9,389,199 B2 | 7/2016 | Cheng et al. |
| 9,458,502 B2 | 10/2016 | Rothberg et al. |
| 9,618,475 B2 | 4/2017 | Rothberg et al. |
| 9,671,363 B2 | 4/2017 | Rothberg et al. |
| 9,823,217 B2 | 11/2017 | Fife et al. |
| 2002/0012933 A1 | 1/2002 | Rothberg et al. |
| 2002/0042388 A1 | 4/2002 | Cooper et al. |
| 2002/0081714 A1 | 6/2002 | Jain et al. |
| 2002/0085136 A1 | 7/2002 | Moon et al. |
| 2002/0150909 A1 | 10/2002 | Stuelpnagel et al. |
| 2002/0168678 A1 | 11/2002 | Williams et al. |
| 2003/0020334 A1 | 1/2003 | Nozu et al. |
| 2003/0044833 A1 | 3/2003 | Elouard et al. |
| 2003/0054396 A1 | 3/2003 | Weiner |
| 2003/0064366 A1 | 4/2003 | Hardin et al. |
| 2003/0068629 A1 | 4/2003 | Rothberg et al. |
| 2003/0108867 A1 | 6/2003 | Chee et al. |
| 2003/0119020 A1 | 6/2003 | Stevens et al. |
| 2003/0124572 A1 | 7/2003 | Umek et al. |
| 2003/0124599 A1 | 7/2003 | Chen et al. |
| 2003/0141928 A1 | 7/2003 | Lee |
| 2003/0141929 A1 | 7/2003 | Casper et al. |
| 2003/0152994 A1 | 8/2003 | Woudenberg et al. |
| 2003/0155942 A1 | 8/2003 | Thewes |
| 2003/0186262 A1 | 10/2003 | Cailloux |
| 2003/0211502 A1 | 11/2003 | Sauer et al. |
| 2003/0215791 A1 | 11/2003 | Garini et al. |
| 2003/0215857 A1 | 11/2003 | Kilger et al. |
| 2003/0224419 A1 | 12/2003 | Corcoran et al. |
| 2003/0227296 A1 | 12/2003 | Lee |
| 2004/0002470 A1 | 1/2004 | Keith et al. |
| 2004/0023253 A1 | 2/2004 | Kunwar et al. |
| 2004/0079636 A1 | 4/2004 | Hsia et al. |
| 2004/0106211 A1 | 6/2004 | Kauer et al. |
| 2004/0121354 A1 | 6/2004 | Yazawa et al. |
| 2004/0130377 A1 | 7/2004 | Takeda et al. |
| 2004/0136866 A1 | 7/2004 | Pontis et al. |
| 2004/0146849 A1 | 7/2004 | Huang et al. |
| 2004/0185484 A1 | 9/2004 | Costa et al. |
| 2004/0185591 A1 | 9/2004 | Hsiung et al. |
| 2004/0197803 A1 | 10/2004 | Yaku et al. |
| 2005/0006234 A1 | 1/2005 | Hassibi |
| 2005/0009022 A1 | 1/2005 | Weiner et al. |
| 2005/0031490 A1 | 2/2005 | Gumbrecht et al. |
| 2005/0032075 A1 | 2/2005 | Yaku et al. |
| 2005/0058990 A1 | 3/2005 | Guia et al. |
| 2005/0093645 A1 | 5/2005 | Watanabe et al. |
| 2005/0095602 A1 | 5/2005 | West et al. |
| 2005/0100939 A1 | 5/2005 | Namsaraev et al. |
| 2005/0106587 A1 | 5/2005 | Klapproth et al. |
| 2005/0151181 A1 | 7/2005 | Beintner et al. |
| 2005/0156207 A1 | 7/2005 | Yazawa et al. |
| 2005/0156584 A1 | 7/2005 | Feng |
| 2005/0181440 A1 | 8/2005 | Chee et al. |
| 2005/0189960 A1 | 9/2005 | Tajima |
| 2005/0191698 A1 | 9/2005 | Chee et al. |
| 2005/0202582 A1 | 9/2005 | Eversmann et al. |
| 2005/0206548 A1 | 9/2005 | Muramatsu et al. |
| 2005/0212016 A1 | 9/2005 | Brunner et al. |
| 2005/0221473 A1 | 10/2005 | Dubin et al. |
| 2005/0230245 A1 | 10/2005 | Morgenshtein et al. |
| 2005/0239132 A1 | 10/2005 | Klapproth |
| 2005/0282224 A1 | 12/2005 | Fouillet et al. |
| 2006/0000772 A1 | 1/2006 | Sano et al. |
| 2006/0024711 A1 | 2/2006 | Lapidus et al. |
| 2006/0035400 A1 | 2/2006 | Wu et al. |

(56) References Cited

U.S. PATENT DOCUMENTS

| | | |
|---|---|---|
| 2006/0038601 A1 | 2/2006 | Giguere |
| 2006/0057025 A1 | 3/2006 | Eversmann et al. |
| 2006/0057604 A1 | 3/2006 | Chen et al. |
| 2006/0141474 A1 | 6/2006 | Miyahara et al. |
| 2006/0154399 A1 | 7/2006 | Sauer et al. |
| 2006/0166203 A1 | 7/2006 | Tooke et al. |
| 2006/0182664 A1 | 8/2006 | Peck et al. |
| 2006/0197118 A1 | 9/2006 | Migliorato et al. |
| 2006/0199193 A1 | 9/2006 | Koo et al. |
| 2006/0199493 A1 | 9/2006 | Hartmann et al. |
| 2006/0205061 A1 | 9/2006 | Roukes |
| 2006/0219558 A1 | 10/2006 | Hafeman et al. |
| 2006/0228721 A1 | 10/2006 | Leamon et al. |
| 2006/0246497 A1 | 11/2006 | Huang et al. |
| 2006/0266946 A1 | 11/2006 | Defrise et al. |
| 2006/0269927 A1 | 11/2006 | Lieber |
| 2006/0289726 A1 | 12/2006 | Paulus et al. |
| 2007/0031291 A1 | 2/2007 | Piech et al. |
| 2007/0087401 A1 | 4/2007 | Neilson et al. |
| 2007/0092872 A1 | 4/2007 | Rothberg et al. |
| 2007/0095663 A1 | 5/2007 | Chou et al. |
| 2007/0096164 A1 | 5/2007 | Peters et al. |
| 2007/0099173 A1 | 5/2007 | Spira et al. |
| 2007/0138128 A1 | 6/2007 | Chodavarapu et al. |
| 2007/0138132 A1 | 6/2007 | Barth |
| 2007/0172865 A1 | 7/2007 | Hardin et al. |
| 2007/0212681 A1 | 9/2007 | Shapiro et al. |
| 2007/0217963 A1 | 9/2007 | Elizarov et al. |
| 2007/0231824 A1 | 10/2007 | Chee et al. |
| 2007/0233477 A1 | 10/2007 | Halowani et al. |
| 2007/0247170 A1 | 10/2007 | Barbaro et al. |
| 2007/0250274 A1 | 10/2007 | Volkov et al. |
| 2007/0262363 A1 | 11/2007 | Tao et al. |
| 2007/0278111 A1 | 12/2007 | Boussaad et al. |
| 2007/0278488 A1 | 12/2007 | Hirabayashi et al. |
| 2008/0003142 A1 | 1/2008 | Link et al. |
| 2008/0014589 A1 | 1/2008 | Link et al. |
| 2008/0047836 A1 | 2/2008 | Strand et al. |
| 2008/0063566 A1 | 3/2008 | Matsumoto et al. |
| 2008/0085219 A1 | 4/2008 | Beebe et al. |
| 2008/0096216 A1 | 4/2008 | Quake |
| 2008/0111161 A1 | 5/2008 | Sorge et al. |
| 2008/0121946 A1 | 5/2008 | Youn et al. |
| 2008/0136933 A1 | 6/2008 | Dosluoglu et al. |
| 2008/0164917 A1 | 7/2008 | Floyd et al. |
| 2008/0178692 A1 | 7/2008 | Jung et al. |
| 2008/0185616 A1 | 8/2008 | Johnson et al. |
| 2008/0204048 A1 | 8/2008 | Stasiak et al. |
| 2008/0205559 A1 | 8/2008 | Iida |
| 2008/0210931 A1 | 9/2008 | Truong et al. |
| 2008/0230386 A1 | 9/2008 | Srinivasan et al. |
| 2009/0048124 A1 | 2/2009 | Leamon et al. |
| 2009/0062132 A1 | 3/2009 | Borner |
| 2009/0075838 A1 | 3/2009 | El Gamal et al. |
| 2009/0079414 A1 | 3/2009 | Levon et al. |
| 2009/0120905 A1 | 5/2009 | Kohl et al. |
| 2009/0121258 A1 | 5/2009 | Arvind |
| 2009/0127689 A1 | 5/2009 | Ye et al. |
| 2009/0149607 A1 | 6/2009 | Karim et al. |
| 2009/0156425 A1 | 6/2009 | Walt et al. |
| 2009/0170728 A1 | 7/2009 | Walt et al. |
| 2009/0194416 A1 | 8/2009 | Hsiung et al. |
| 2009/0273386 A1 | 11/2009 | Korobeynikov et al. |
| 2009/0299138 A1 | 12/2009 | Mitsuhashi |
| 2010/0007326 A1 | 1/2010 | Nakazato |
| 2010/0026814 A1 | 2/2010 | Shimoda |
| 2010/0039146 A1 | 2/2010 | Park et al. |
| 2010/0052765 A1 | 3/2010 | Makino |
| 2010/0105373 A1 | 4/2010 | Kanade |
| 2010/0133547 A1 | 6/2010 | Kunze et al. |
| 2010/0137143 A1 | 6/2010 | Rothberg et al. |
| 2010/0176463 A1 | 7/2010 | Koizumi et al. |
| 2010/0244106 A1 | 9/2010 | Parker et al. |
| 2010/0273166 A1 | 10/2010 | Garcia |
| 2010/0301398 A1 | 12/2010 | Rothberg et al. |
| 2011/0037121 A1 | 2/2011 | Lee et al. |
| 2011/0062972 A1 | 3/2011 | Je et al. |
| 2011/0114827 A1 | 5/2011 | Yamaoka et al. |
| 2011/0165557 A1 | 7/2011 | Ah et al. |
| 2011/0169056 A1 | 7/2011 | Wey et al. |
| 2011/0181253 A1 | 7/2011 | Isham et al. |
| 2011/0236263 A1* | 9/2011 | Sawada .............. G01N 21/8507 422/82.01 |
| 2011/0248320 A1 | 10/2011 | Rothberg et al. |
| 2011/0262903 A1 | 10/2011 | Davidson et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0287945 A1 | 11/2011 | Rothberg et al. |
| 2011/0299337 A1 | 12/2011 | Parris et al. |
| 2012/0001056 A1 | 1/2012 | Fife et al. |
| 2012/0001236 A1 | 1/2012 | Fife et al. |
| 2012/0001237 A1 | 1/2012 | Fife et al. |
| 2012/0001615 A1 | 1/2012 | Levine et al. |
| 2012/0001646 A1 | 1/2012 | Bolander et al. |
| 2012/0013392 A1 | 1/2012 | Rothberg et al. |
| 2012/0034607 A1 | 2/2012 | Rothberg et al. |
| 2012/0045368 A1 | 2/2012 | Hinz et al. |
| 2012/0055811 A1 | 3/2012 | Rothberg et al. |
| 2012/0055813 A1 | 3/2012 | Rothberg et al. |
| 2012/0056248 A1 | 3/2012 | Fife |
| 2012/0060587 A1 | 3/2012 | Babcock et al. |
| 2012/0067723 A1 | 3/2012 | Rearick et al. |
| 2012/0129703 A1 | 5/2012 | Rothberg et al. |
| 2012/0129732 A1 | 5/2012 | Rothberg et al. |
| 2012/0135870 A1 | 5/2012 | Rothberg et al. |
| 2012/0143531 A1 | 6/2012 | Davey et al. |
| 2012/0154018 A1 | 6/2012 | Sugiura |
| 2012/0161207 A1 | 6/2012 | Homyk et al. |
| 2012/0168307 A1 | 7/2012 | Fife |
| 2012/0173159 A1 | 7/2012 | Davey et al. |
| 2012/0249192 A1 | 10/2012 | Matsushita et al. |
| 2012/0261274 A1 | 10/2012 | Rearick et al. |
| 2012/0265474 A1 | 10/2012 | Rearick et al. |
| 2012/0286771 A1 | 11/2012 | Rothberg et al. |
| 2012/0326213 A1 | 12/2012 | Bustillo et al. |
| 2012/0326767 A1 | 12/2012 | Milgrew |
| 2012/0329043 A1 | 12/2012 | Milgrew |
| 2012/0329192 A1 | 12/2012 | Bustillo et al. |
| 2013/0001653 A1 | 1/2013 | Milgrew et al. |
| 2013/0004948 A1 | 1/2013 | Milgrew et al. |
| 2013/0009214 A1 | 1/2013 | Bustillo et al. |
| 2013/0027594 A1 | 1/2013 | Krymski |
| 2013/0056353 A1 | 3/2013 | Nemirovsky et al. |
| 2013/0105868 A1 | 5/2013 | Kalnitsky et al. |
| 2013/0135018 A1 | 5/2013 | Kuo et al. |
| 2013/0189790 A1 | 7/2013 | Li et al. |
| 2013/0210128 A1 | 8/2013 | Rothberg et al. |
| 2013/0210182 A1 | 8/2013 | Rothberg et al. |
| 2013/0210641 A1 | 8/2013 | Rothberg et al. |
| 2013/0217004 A1 | 8/2013 | Rothberg et al. |
| 2013/0217587 A1 | 8/2013 | Rothberg et al. |
| 2013/0281307 A1 | 10/2013 | Li et al. |
| 2013/0341734 A1 | 12/2013 | Merz |
| 2014/0075237 A1 | 3/2014 | Ware |
| 2014/0080717 A1 | 3/2014 | Li et al. |
| 2014/0148345 A1 | 5/2014 | Li et al. |
| 2014/0234981 A1 | 8/2014 | Zarkesh-Ha et al. |
| 2014/0235463 A1 | 8/2014 | Rothberg et al. |
| 2014/0308752 A1 | 10/2014 | Chang et al. |
| 2014/0364320 A1 | 12/2014 | Rothberg et al. |
| 2014/0367748 A1 | 12/2014 | Dalton et al. |
| 2014/0367750 A1 | 12/2014 | Fife |
| 2015/0097214 A1 | 4/2015 | Chen et al. |
| 2016/0097736 A1 | 4/2016 | Fife |
| 2016/0178568 A1 | 6/2016 | Cheng et al. |
| 2017/0038334 A1 | 2/2017 | Barbee |
| 2017/0059514 A1 | 3/2017 | Hoffman |
| 2017/0102356 A1 | 4/2017 | Lin |

FOREIGN PATENT DOCUMENTS

| | | |
|---|---|---|
| DE | 4232532 | 4/1994 |
| DE | 4430811 | 9/1995 |

(56) References Cited

FOREIGN PATENT DOCUMENTS

| | | |
|---|---|---|
| DE | 102004044299 | 3/2006 |
| DE | 102008012899 | 9/2009 |
| EP | 1243925 | 9/2002 |
| EP | 1371974 | 12/2003 |
| EP | 1542009 | 6/2005 |
| EP | 1669749 | 6/2006 |
| EP | 1870703 | 12/2007 |
| EP | 1975246 | 10/2008 |
| JP | 58070155 | 4/1983 |
| JP | 62237349 | 10/1987 |
| JP | 02250331 | 10/1990 |
| JP | 02310931 | 12/1990 |
| JP | H05080115 | 4/1993 |
| JP | H10-078827 | 3/1998 |
| JP | 2000055874 | 2/2000 |
| JP | 2002-221510 | 8/2002 |
| JP | 2002272463 | 9/2002 |
| JP | 2003004697 | 1/2003 |
| JP | 2003279532 | 10/2003 |
| JP | 2003-322633 | 11/2003 |
| JP | 2004-00033 | 1/2004 |
| JP | 2004-271384 | 9/2004 |
| JP | 2004-343441 | 12/2004 |
| JP | 2005515475 | 5/2005 |
| JP | 2006-138846 | 6/2006 |
| JP | 2006284225 | 10/2006 |
| JP | 2007-512810 | 5/2007 |
| JP | 2007243003 | 9/2007 |
| JP | 2008-215974 | 9/2008 |
| JP | WO2009/081890 | * 7/2009 |
| JP | 2015-506557 | 3/2012 |
| KR | 100442838 | 8/2004 |
| KR | 100455283 | 11/2004 |
| TW | 200510714 | 3/2005 |
| TW | 200946904 | 11/2009 |
| WO | WO-1989/009283 | 10/1989 |
| WO | WO-1990/005910 | 5/1990 |
| WO | WO-1998/013523 | 4/1998 |
| WO | WO-1998/046797 | 10/1998 |
| WO | WO-1999/019717 | 4/1999 |
| WO | WO-2001/042498 | 6/2001 |
| WO | WO-2001/081896 | 11/2001 |
| WO | WO-2002/24322 | 3/2002 |
| WO | WO-2002/077287 | 10/2002 |
| WO | WO-2004/017068 | 2/2004 |
| WO | WO-2004/040291 | 5/2004 |
| WO | WO-2004/048962 | 6/2004 |
| WO | WO-2004081234 | 9/2004 |
| WO | WO-2005/015156 | 2/2005 |
| WO | WO-2005/054431 | 6/2005 |
| WO | WO-2005/062049 | 7/2005 |
| WO | WO-2005/084367 | 9/2005 |
| WO | WO-2005/090961 | 9/2005 |
| WO | WO-2006/056226 | 6/2006 |
| WO | WO-2007/002204 | 1/2007 |
| WO | WO-2008/058282 | 5/2008 |
| WO | WO-2008/107014 | 9/2008 |
| WO | WO-2008/133719 | 11/2008 |
| WO | WO-2009/014155 | 1/2009 |
| WO | WO-2009/041917 | 4/2009 |
| WO | WO-2009/158006 | 12/2009 |
| WO | WO-2010/047804 | 4/2010 |
| WO | WO-2010/138186 | 12/2010 |
| WO | WO-2012/046137 | 4/2012 |
| WO | WO-2012/152308 | 11/2012 |
| WO | WO-2014/077783 | 5/2014 |

OTHER PUBLICATIONS

[No Author Listed], "ISFET Wikipedia article", *Wikipedia*, Last modified Nov. 7, 2006.
Ahmadian et al., "Single-nucleotide polymorphism analysis by pyrosequencing", *Analytical Biochemistry*, vol. 280, No. 1, Apr. 2000, 103-110.
Akiyama et al., "Ion-Sensitive Field-Effect Transistors with Inorganic Gate Oxide for pH Sensing", *IEE Transactions on Electron Devices*, vol. 29, No. 12, Dec. 1982, 1936-1941.
Anderson et al., "A system for multiplexed direct electrical detection of DNA synthesis", *Sensors and Actuators B : Chemical*, vol. 129, No. 1, Jan. 2008, 79-86.
AU2011226767, Search Information Statement, dated Oct. 26, 2011.
Bandiera et al., "A fully electronic sensor for the measurement of cDNA hybridization kinetics", *Biosensors and Bioelectronics*, vol. 22, Nos. 9-10, Apr. 15, 2007, 2108-2114.
Bandettini et al., "Processing Strategies for Time-Course Data Sets in Functional MRI of the Human Brain," MRM, vol. 30, 1993, pp. 161-172.
Barbaro et al., "Fully electronic DNA hybridization detection by a standard CMOS biochip", *Sensors and Actuators B : Chemical*, vol. 118, Nos. 1-2, Oct. 25, 2006, 41-46.
Barbaro et al., "A CMOS, Fully Integrated Sensor for Electronic Detection of DNA Hybridization", *IEEE Electron Device Letters*, vol. 27, No. 7, 2006, 595-597.
Barbaro et al., "A Charge-Modulated FET for Detection of Biomolecular Processes: Conception, Modeling, and Simulation", *IEEE Transactions on Electron Devices*, vol. 53, No. 1, 2006, 158-166.
Bashford et al., "Automated bead-trapping apparatus and control system for single-molecule DNA sequencing", *Optics Express*, vol. 16, No. 5, Mar. 3, 2008, 3445-3455.
Baumann et al., "Microelectronic sensor system for microphysiological application on living cells", *Sensors and Actuators B: Chemical*, vol. 55, 1999, 77-89.
Bausells, J. et al., "Ion-sensitive field-effect transistors fabricated in a commercial CMOS technology", *Sensors and Actuators B : Chemical*, vol. 57, 1999, 56-62.
Beer et al., "Anion Recognition and Sensing: The State of the Art and Future Perspectives", *Angew. Chem. Int. Ed.*, vol. 40, 2001, 487-516.
Bergveld, "ISFET, Theory and Practice", *IEEE Sensor Conference*, Toronto, Oct. 2003, 1-26.
Bergveld, "Thirty years of ISFETOLOGY What happened in the past 30 years and what may happen in the next 30 ears", *Sensors and Actuators B : Chemical*, vol. 88, 2003, 1-20.
Besselink et al., "ISFET Affinity Sensor", *Methods in Biotechnology, vol. 7: Affinity Biosensors: Techniques and Protocols*, 1998, 173-185.
Bobrov et al., "Chemical sensitivity of an ISFET with Ta2O5 membrane in strong acid and alkaline solutions", *Sensors and Actuators B: Chemical*, vol. 3, 1991, 75-81.
Bockelmann et al., "Detecting DNA by field effect transistor arrays", *Proceedings of the 2006 IFIP International Conference on Very Large Scale Integration*, 2006, 164-168.
Bousse et al., "A process for the combined fabrication of ion sensors and CMOS circuits", *IEEE Electron Device Letters*, vol. 9, No. 1, 1988, 44-46.
Bousse et al., "Zeta potential measurements of Ta2O5 and SiO2 thin films" *Journal of Colloid and Interface Science*, vol. 147, No. 1, 1991, 22-32.
Brenner et al., "Gene expression analysis by massively parallel signature sequencing (MPSS) on microbead arrays", *Nature Biotechnology*, vol. 18, No. 6, Jun. 2000, 630-634.
Brzozka et al., "Enhanced performance of potassium CHEMFETs by optimization of a polysiloxane membrane", *Sensors and Actuators B: Chemical*, vol. 18, Nos. 1-3, Mar. 1994, 38-41.
Chan et al., "An Integrated ISFETs Instrumentation System in Standard CMOS Technology", *IEEE Journal of Solid-State Circuits*, vol. 45, No. 9, Sep. 2010, 1923-1934.
Chen et al., "Nanoscale field effect transistor for biomolecular signal amplification", *Applied Physics Letters*, vol. 91, No. 24, Dec. 2007, 243511-1-243511-3.
Chen et al., "Silicon-based nanoelectronic field-effect pH sensor with local gate control", *Applied Physics Letters*, vol. 89, 2006, 223512-1-223512-3.

(56) References Cited

OTHER PUBLICATIONS

Chin et al., "Titanium Nitride Membrane Application to Extended Gate Field Effect Transistor pH Sensor Using VLSI Technology", *Japanese Journal Applied Physics*, vol. 40, Part 1, No. 11, Nov. 2001, 6311-6315.
Chou et al., "Letter to the Editor on Simulation of Ta2O5 gate ISFET temperature characteristics", *Sensors and Actuators B: Chemical*, vol. 80, 2001, 290-291.
Chou et al., "Simulation of Ta2O5 gate ISFET temperature characteristics", *Sensor and Actuators B: Chemical*, vol. 71, 2000, 73-76.
Chung et al., "ISFET interface circuit embedded with noise rejection capability", *Electronics Letters*, vol. 40, No. 18, Oct. 2004, 1115-1116.
Chung et al., "ISFET performance enhancement by using the improved circuit techniques", *Sensors and Actuators B: Chemical*, vol. 113, No. 1, Jan. 2006, 555-562.
Chung et al., "New ISFET interface circuit design with temperature compensation", *Microelectronics Journal*, vol. 37, No. 10, Oct. 1, 2006, 1105-1114.
Chung et al., "Temperature compensation electronics for ISFET readout applications", *Biomedical Circuits and Systems*, IEEE International Workshop Singapore, Dec. 1, 2004, 305-308.
Cobben et al., "Transduction of Selective Recognition of Heavy Metal Ions by Chemically Modified Field Effect Transistors (CHEMFETs)" *Journal of the American Chemical Society*, vol. 114, No. 26, 1992, 10573-10582.
Dahl et al., "Circle-to-circle amplification for precise and sensitive DNA analysis," Proceedings of the National Academy of Sciences, vol. 101, No. 13, Mar. 2004, pp. 4548-4553.
Dazhong et al., "Research of CMOS Biosensor IC for Extracellular Electrophysiological Signal Recording and pH value Measuring", *Solid-State and Integrated-Circuit Technology, 9th International Conference*, NJ USA, Oct. 20, 2008, 2557-2560.
Dorf, "The Electrical Engineering Handbook", *University of California, Davis, CRC Press, 2 Edition, Chapter 3—Linear Circuit Analysis*, Jun. 25, 2004, 3-1 to 3-66.
Eastman Kodak Company, "Image Sensor Solutions-Full-Frame CCD Image Sensor Performance Specification", www.physics.csbsju.edu/370/photometry/manuals/kaf-1001e.pdf, Feb. 19, 2001.
Eijkel et al., "Measuring Donnan-related phenomena using a solid-state ion sensor and a concentration-step method", *Journal of Membrane Science*, vol. 127, No. 2, May 1997, 203-221.
Eijkel, "Potentiometric detection and characterization of adsorbed protein using stimulus-response measurement techniques", *Thesis*, Sep. 3, 1955, 1-47 and 160-192.
Eltoukhy et al., "A 0.18um CMOS 10-6 lux Bioluminescence Detection System-on-Chip", *ISSCC 2004/Session 12/Biomicrosystems/12.3*, 2004, 1-3.
Eltoukhy et al., "A. 0.18-um CMOS Bioluminescence Detection Lab-on-Chip" *IEEE J Solid-State Circuits*, vol. 41, No. 3, 2006, 651-662.
EP09798251.6, Extend Search Report, dated Aug. 27, 2013, 6 pages.
EP09822323.3, Extended Search Report, dated May 27, 2015, 8 pages.
EP10780930.3, Search Report, dated Jun. 15, 2015, 3 pages.
EP10780935.2, Search Report, dated Jun. 9, 2015, 5 pages.
EP10780935.2 Supplementary Search Report, dated Sep. 30, 2015, 6 pages.
EP10857377.5, Search Report, dated Jun. 26, 2015, 3 pages.
EP11801437.2, Extended Search Report, dated Jul. 25, 2013, 10 pages.
EP11801439.8 Extended Search Report, dated Mar. 7, 2014, 9 pages.
EP11804218.3, Extended Search Report, dated Jul. 11, 2013, 3 pages.
EP11827128.7, Search Report, dated Aug. 1, 2013, 5 pages.
EP13161312.7, Extend Search Report, dated Oct. 15, 2013, 8 pages.
EP13163995.7, Search Report, dated Jul. 9, 2014.
EP13163995.7, Extend European Search Report, dated Aug. 20, 2013, 6 pages.
EP13164768.7,, Search Report, dated Aug. 20, 2013, 6 pages.
EP13174555.6, Extended Search Report, dated Dec. 12, 2013, 8 pages.
EP13174555.6, Search Report, dated Nov. 21, 2013, 5 pages.
EP13177039.8, Search Report, dated Nov. 21, 2013, 9 pages.
EP13177590.0, Search Report, dated Nov. 20, 2013, 5 pages.
EP14152861.2, Search Report, dated Jul. 7, 2014, 5 pages.
EP15170247.9, Search Report, dated Nov. 10, 2015, 4 pages.
EP17167536.6, Search Report, dated Nov. 7, 2017, 1-13.
Eriksson et al, "Pyrosequencing technology at elevated temperature", *Electrophoresis*, vol. 25, No. 1, Jan. 2004, 20-27.
Esfandyarpour et al., "Gate-controlled microfluidic chamber with magnetic bead for DNA sequencing-by-synthesis technology", *Proc 5th Intl Conf Nanochannels, Microchannels, Minnichannels*, Puebla, Mexico (Jun. 18-20, 2007), 1-5.
Eversmann et al., "A 128 × 128 CMOS Biosensor Array for Extracellular Recording of Neural Activity", *IEEE Journal Solid-State Circuit*, vol. 38, No. 12, Dec. 12, 2003, 2306-2317.
Faramarzpour et al., "CMOS-Based Active Pixel for Low-Light Level Detection: Analysis and Measurements", *IEEE Transactions on Electron Devices*, vol. 54, No. 12, Dec. 2007, 3229-3237.
Finn et al., "Towards an Optimization of FET-Based Bio-Sensors", *European Cells and Materials*, vol. 4, Sup 2, 2002, 21-23.
Fraden, "Handbook of Modern Sensors—Physics, Designs, and Applications . . . ", *17.3.2 CHEMFET Sensors*, 1996, 499-501.
Fritz et al., "Electronic detection of DNA by its intrinsic molecular charge", *PNAS*, vol. 99, No. 22, Oct. 2002, 14142-14146.
Gardner et al., "Enhancing electronic nose performance by sensor selection using a new integer-based genetic algorithm approach", *Sensors and Actuators B: Chemical*, vol. 106, 2005, 114-121.
GB0811656.8, Search and Examination Report, dated Mar. 12, 2010.
GB0811656.8, Search Report, dated Sep. 21, 2009.
GB0811657.6, Search Report, dated Oct. 27, 2009.
Gracia et al., "Test Structures for ISFET Chemical Sensors" *Proc IEEE 1992 Intl Conf Microelec Test Struct*, vol. 5, 1992, 156-159.
Hammond et al., "Design of a Single-Chip pH Sensor Using a Conventional 0.6—µm CMOS Process", *IEEE Sensors Journal*, vol. 4, No. 6, 2004, 706-712.
Hammond et al., Performance and system-on-chip integration of an unmodified CMOS ISFET, *Science Dairect, Sensors and Actuators B: Chemical*, vols. 111-112, Nov. 2005, 254-258.
Hammond et al., "A System-on-Chip Digital pH Meter for Use in a Wireless Diagnostic Capsule", *IEEE Transactions on Biomedical Engineering*, vol. 52, No. 4, Apr. 2005, 687-694.
Hammond et al., "Encapsulation of a liquid-sensing microchip using SU-8 photoresist", *MicoElectronic Engineering*, vols. 73-74, 2004, 893-897.
Hammond et al., "Genomic sequencing and analysis of a Chinese Hamster ovary cell line using Illumina sequencing technology", *BMC Genomics*, vol. 12, No. 67, 2011, 1-8.
Han, "Label-free detection of biomolecules by a field-effect transistor microarray biosensor with bio-functionalized gate surfaces", *Masters Dissertation*, 2006, 1-63.
Han et al., "Detection of DNA hybridization by a field-effect transistor with covalently attached catcher molecules", *Surface and Interface Analysis*, vol. 38, 2006, 176-181.
Hanshaw et al., "An indicator displacement system for fluorescent detection of phosphate oxyanions under physiological conditions", *Tetrahedron Letters*, vol. 45, Nov. 15, 2004, 8721-8724.
Hara et al., "Dynamic response of a $Ta_2O_5$-gate pH-sensitive field-effect transistor", *Sensors Actuators B: Chemical*, vol. 32, May 1996, 115-119.
Hermon et al., "Miniaturized bio-electronic hybrid for chemical sensing applications" *Tech Connect News*, Apr. 22, 2008, 1.
Hideshima et al., "Detection of tumor marker in blood serum using antibody-modified field effect transistor with optimized BSA blocking", *Sensors and Actuations B: Chemical*, vol. 161, No. 1, Jan. 2012, 146-150.

(56) References Cited

OTHER PUBLICATIONS

Hijikata et al., "Identification of a Single Nucleotide Polymorphism in the MxA Gene Promoter (T/T at nt-88) Correlated with the Response of Hepatitis C Patients to Interferon", *Intervirology*, vol. 43, No. 2, Aug. 2000, 124-127.
Hizawa et al., "Fabrication of a two-dimensional pH image sensor using a charge transfer technique", *Sensors and Actuators B: Chemical*, vol. 117, No. 2, Oct. 2006, 509-515.
Hizawa et al., "Sensing Characteristics of Charge Transfer Type pH Sensor by Accumulative Operation", *IEEE Sensors*. EXCO, Daegu, Korea, Oct. 22-25, 2006, 144-147.
Hizawa et al., "32 × 32 pH Image Sensors for Real Time Observation of Biochemical Phenomena", *Transducers & Eurosensors '07*, 14th Intl. Conf. on Solid-State, Actuators and Microsystems, Lyon, France, Jun. 10-14, 2007, 2007, pp. 1311-1312.
Ingebrandt et al., "Label-free detection of DNA using field-effect transistors", *Physica Status Solidi a*, vol. 203, No. 14, Nov. 2006, 3399-3411.
Izuru, "Kojien", *published by Owanami, Fourth Edition*, with English Translation, 1991, 2683.
Jakobson et al., "Low frequency noise and drift in Ion Senstive Field Effect Transistors", *Sensors Actuators B: Chemical*, vol. 68, Nos. 1-3, Aug. 2000, 134-139.
Ji et al., "A CMOS contact imager for locating individual cells", *ISCAS*, 2006, 3357-3360.
Ji et al., "Contact Imaging: Simulation and Experiment", *IEEE Trans Circuits Systems-I: Regular Papers*, vol. 54, No. 8, Jul. 2007, 1698-1710.
Kim et al., "An FET-type charger sensor for highly sensitive detection of DNA sequence", *Biosensors and Bioelectronics*, vol. 20, No. 1, Jul. 2004, 69-74.
Klein, "Time effects of ion-sensitive field-effect transistors" *Sensors and Actuators B: Chemical*, vol. 17, Nos. 1-2, May 1989, 203-208.
Koch et al., "Protein detection with a novel ISFET-based zeta potential analyzer" *Biosensors & Bioelectronics*, vol. 14, No. 4, Apr. 1999, 413-421.
Krause et al., "Extended gate electrode arrays for extracellular signal recordings", *Sensors and Actuators B: Chemical*, vol. 70, Nos. 1-3, Nov. 2000, 101-107.
Kruise et al., "Detection of protein concentrations using a pH-step titration method" *Sensors Actuators B: Chemical*, vol. 44, Nos. 1-3, Oct. 1997, 297-303.
Leamon et al., A Massively Parallel Pico TiterPlate Based Platform for Discrete Picoliter-Scale Polymerase Chain Reactions, *Electrophoresis*, vol. 24, No. 21, Nov. 2003, 3769-3777.
Leamon et al.,"Cramming More Sequencing Reactions onto Microreactor Chips", *Chemical Reviews*, vol. 107, No. 8, Aug. 2007, 3367-3376.
Lee et al., "Ion-sensitive Field-Effect Transistor for Biological Sensing", *Sensors*, vol. 9, 2009, 7111-7131.
Lee et al., "An Enhanced Glucose Biosensor Using Charge Transfer Techniques" *Biosensors and Bioelectronics*, vol. 24, No. 4, Dec. 2008, 650-656.
Li et al., "Sequence-Specific Label-Free DNA Sensors Based on Silico Nanowires", *Nano Letters,*, vol. 4, No. 2, Jan. 2004, 245-247.
Ligler et al., "Array biosensor for detection of toxins", *Analytical and Bioanalytical Chemistry*, vol. 377, No. 3, Oct. 2003, 469-477.
Lin et al., "Practicing the Novolac deep-UV portable conformable masking technique" *Journal of Vacuum Science and Technology*, Vo. 19, No. 4, 1981, 1313-1319.
Liu et al., "An ISFET based sensing array with sensor offset compensation and pH sensitivity enhancement" *Proc. of 2010 IEEE Int. Symp. on Circuits and Systems (ISCAS)*, ISBN:978-1-4244-5308-5, Jun. 2, 2010, 2283-2286.
Lohrengel et al., "A new microcell or microreactor for material surface investigations at large current densities", *Electrochimica Acta*, vol. 49, Nos. 17-18, Jul. 2004, 2863-2870.
Lui et al., "A Test Chip for ISFET/CMNOS Technology Development", *Proc. of the 1996 IEEE Intl. Conf. on Microelectronic Test Structures*, vol. 9, Aug. 1996, 123-128.

Maki et al., "Nanowire-transistor based ultra-sensitive DNA methylation detection" *Biosensors & Bioelectronics*, vol. 23, No. 6, Jan. 2008, 780-787.
Margulies et al., "Genome sequencing in microfabricated high-density picolitre reactors", *Nature*, vol. 437, No. 15, Jul. 31, 2005, 376-380.
Marshall et al., "DNA chips: an array of possibilities", *Nature Biotechnology*, vol. 16, No. 1, Jan. 1998, 27-31.
Martel et al., "Single- and multi-wall carbon nanotube field-effect transistors", *Applied Physics Letters*, vol. 73, No. 17, Oct. 1998, 2447-2449.
Martinoia et al., "Development of ISFET Array-Based Microsystems for Bioelectrochemical measurements of cell populations", *Biosensors & Bioelectronics*, vol. 16, Nos. 9-12, Dec. 2001, 1043-1050.
Martinoia et al., "A behavioral macromodel of the ISFET in SPICE" *Sensors and Actuators B : Chemical*, vol. 62, No. 3, Mar. 2000, 182-189.
Matsuo et al., "Charge Transfer Type pH Sensor with Super High Sensitivity", *the 14th international conference on solid-state sensors actuators and microsystems*, France, Jun. 10-14, 2007, 1881-1884.
Matula, "Electrical Resistivity of Copper, Gold, Palladium, and Silver", *Journal of Physical and Chemical Reference Data*, vol. 8, No. 4, 1979, 1147-1298.
Medoro et al., "A Lab-on-a-Chip for Cell Detection and Manipulation" *IEEE Sensors Journal*, vol. 3, No. 3, 2003, 317-325.
Meyburg, et al., "N-Channel field-effect transistors with floating gates for extracellular recordings", *Biosensors and Bioelectronics*, vol. 21, No. 7, Jan. 2006, 1037-1044.
Milgrew et al., "A large transistor based sensor array chip for direct extracellular imaging", *Sensors and Actuators B: Chemical*, vols. 111-112, Nov. 2005, 347-353.
Milgrew et al., "The development of scalable sensor arrays using standard CMOS technology", *Sensors and Actuators B: Chemical*, vol. 103, Nos. 1-2, Sep. 2004, 37-42.
Milgrew et al., "The fabrication of scalable multi-sensor arrays using standard CMOS technology", *IEEE Custom Integrated Circuits Conference*, 2003, 513-516.
Milgrew et al., "A 16 × 16 CMOS proton camera array for direct extracellular imaging of hydrogen-ion activity", *IEEE Intl Solid-State Circuits Conf*, Session vol. 32, No. 24, Mar. 2008, 590-591;638.
Milgrew et al., "Matching the transconductance characteristics of CMOS ISFET arrays by removing trapped charge", *IEEE Transactions on Electronic Devices*, vol. 55, No. 4, Apr. 2008, 1074-1079.
Milgrew et al., "Microsensor Array Technology for Direct Extracellular Imaging", Electronics Design Centre, Department of Electronics and Electrical Engineering, University of Glasgow, Apr. 5, 2006, 1-23.
Milgrew et al., "A Proton Camera Array Technology for Direct Extracellular Ion Imaging", *IEEE International Symposium on Industrial Electronics*, 2008, 2051-2055.
Miyahara et al., "Biochip Using Micromachining Technology" *J. Institute of Electrostatics*, Japan, vol. 27, No. 6, 2003, 268-272.
Miyahara et al., "Direct Transduction of Primer Extension into Electrical Signal Using Genetic Field Effect Transistor", *Micro Total Analysis Systems*, vol. 1, 2004, 303-305.
Miyahara, Y. et al., "Potentiometric Detection of DNA Molecules Using Field Effect Transistor", *The Japan Society of Applied Physics*, No. 3 (Translation included), 2003, 1180, 30A-S2.
Morgenshtein et al., "Wheatstone-Bridge readout interface for ISFET/REFET applications", *Sensors and Actuators B. Chemical*, vol. 98, No. 1, Mar. 2004, 18-27.
Moriizumi, "Biosensors" *Oyo Buturi (monthly publication of the Japan Society of Applied Physics)*, vol. 54, No. 2, Feb. 10, 1985, 98-114.
Naidu et al., "Introduction to Electrical Engineering" *Chapter 1—Fundamental Concepts of Electricity, McGraw Hill Education (India) Private Limited*, 1995, 1-10.
Nakazato et al., "28p-Y-7 ISFET sensor array integrated circuits based on standard CMOS process", *The 55th annual meeting of the Japan Society of Applied Physics, book of Abstracts*, ISBN:978-4-903968-44-5, Mar. 27, 2008, 70.

(56) References Cited

OTHER PUBLICATIONS

Nakazato, "An Integrated ISFET Sensor Array", *Sensors*, No. 11, ISSN:1424-8220, [online], Internet, URL, http://www.mdpi.com/1424-8220/9/11/8831/pdf, vol. 9, Nov. 2009, 8831-8851.
Neaman, "Electronic Circuit Analysis and Design", *McGraw Hill Higher Education, 2nd edition, Chapter 6—Basic FET Amplifiers*, (reference will be uploaded in 2 parts due to size) Part 1 of 2, Dec. 1, 2000, 313-345.
Neaman, "Electronic Circuit Analysis and Design", *McGraw Hill Higher Education, 2nd edition, Chapter 6—Basic FET Amplifiers*, (reference will be uploaded in 2 parts due to size) Part 2 of 2, Dec. 1, 2000, 46-381.
Nishiguchi et al., "Si nanowire ion-sensitive field-effect transistors with a shared floating gate", *Applied Physics Letters*, vol. 94, No. 16, Apr. 2009, 63106-1 to 163106-3.
Nyren et al., "Enzymatic Method for Continuous Monitoring of Inorganic Pyrophosphate Synthesis", *Analytical Biochemistry*, vol. 151, No. 2, Dec. 1985, 504-509.
Oelbner et al., "Encapsulation of ESFET sensor chips", *Sensors and Actuators B: Chemical*, vol. 105, No. 1, Feb. 2005, 104-117.
Oelbner et al., "Investigation of the dynamic response behaviour of ISFET pH sensors by means of laser Doppler velocimetry (LDV)", *Sensors and Actuators B: Chemical*, vols. 26, Nos. 1-3, Jun. 1995, 345-348.
Offenhausser et al., "Field-Effect transistor array for monitoring electrical activity from mammalian neurons in culture", *Biosensors & Bioelectronics*, vol. 12, No. 8, Jul. 1997, 819-826.
Ohno et al., "Electrolyte-Gated Graphene Field-Effect Transistors for Detecting pH and Protein Adsorption", *Nano Letters*, vol. 9, No. 9, Jul. 28, 2009, 3318-3322.
Palan et al., "New ISFET sensor interface circuit for biomedical applications", *Sensors and Actuators B: Chemical*, vol. 57, Nos. 1-3, Sep. 1999, 63-68.
Park et al., "ISFET glucose sensor system with fast recovery characteristics by employing electrolysis", *Sensors and Actuators B: Chemical*, vol. 83, Nos. 1-3, Mar. 2002, 90-97.
Patolsky et al., "Nanowire-Based Biosensors", *Analytical Chemistry*, vol. 78, No. 13, Jul. 2006, 4261-4269.
PCT/JP2005/001987, International Search Report, dated Apr. 5, 2005.
PCT/JP2005/015522 International Preliminary Report on Patentability, dated Mar. 19, 2007.
PCT/JP2005/015522, International Search Report, dated Sep. 27, 2005.
PCT/US/2009/05745, International Preliminary Report on Patentability, dated Apr. 26, 2011.
PCT/US/2009/05745, International Search Report and Written Opinion, dated Dec. 11, 2009.
PCT/US2007/025721, Declaration of Non-Establishment of International Search Report, dated Jul. 15, 2008.
PCT/US2007/025721, International Preliminary Report on Patentability, dated Jun. 16, 2009.
PCT/US2007/025721, Written Opinion, dated Jun. 16, 2009.
PCT/US2009/003766, International Preliminary Report on Patentability, dated Jan. 5, 2011.
PCT/US2009/003766, International Search Report and Written Opinion, dated Apr. 8, 2010.
PCT/US2009/003797, International Search Report and Written Opinion, dated Mar. 12, 2010.
PCT/US2010/001543, International Preliminary Report on Patentability, dated Nov. 29, 2011.
PCT/US2010/001543, International Search Report and Written Opinion, dated Oct. 13, 2010
PCT/US2010/001547, International Preliminary Report on Patentability, dated Nov. 29, 2011.
PCT/US2010/001547, International Search Report and Written Opinion, dated Aug. 5, 2010.
PCT/US2010/001553, International Preliminary Report on Patentability, dated Dec. 8, 2011.
PCT/US2010/001553, International Search Report and Written Opinion, dated Jul. 28, 2010.
PCT/US2010/048835, International Preliminary Report on Patentability, dated Mar. 19, 2013.
PCT/US2010/048835, International Search Report and Written Opinion, dated Dec. 16, 2010.
PCT/US2011/042655, International Search Report, dated Oct. 21, 2011.
PCT/US2011/042660, International Search Report, dated Nov. 2, 2011.
PCT/US2011/042665, International Search Report, dated Nov. 2, 2011.
PCT/US2011/042668, International Preliminary Report on Patentability, dated Mar. 26, 2013.
PCT/US2011/042668, International Search Report, dated Oct. 28, 2011.
PCT/US2011/042669, International Search Report and Written Opinion, dated Jan. 9, 2012.
PCT/US2011/042683, International Preliminary Report on Patentability, dated Jun. 4, 2013.
PCT/US2011/042683, International Search Report and Written Opinion, dated Feb. 16, 2012.
PCT/US2012/058996, International Search Report and Written Opinion, dated Jan. 22, 2013.
PCT/US2012/071471, International Preliminary Report on Patentability, dated Jun. 24, 2014.
PCT/US2012/071471, International Search Report and Written Opinion, dated Apr. 24, 2013.
PCT/US2012/071482, International Preliminary Report on Patentability, dated Jun. 24, 2014.
PCT/US2012/071482, International Search Report and Written Opinion, dated May 23, 2013.
PCT/US2013/022129, International Preliminary Report on Patentability, dated Jul. 22, 2014.
PCT/US2013/022129, International Search Report and Written Opinion, dated Aug. 9, 2013.
PCT/US2013/022140, International Preliminary Report on Patentability, dated Jul. 22, 2014.
PCT/US2013/022140, International Search Report and Written Opinion, dated May 2, 2013.
PCT/US2014/020887, International Preliminary Report on Patentability, dated Sep. 15, 2015.
PCT/US2014/020887, International Search Report and Written Opinion, dated May 30, 2014.
PCT/US2014/020892, International Search Report and Written Opinion, dated Jun. 3, 2014.
PCT/US2014/040923, International Preliminary Report on Patentability, dated Dec. 15, 2015.
PCT/US2014/040923, International Search Report and Written Opinion, dated Sep. 1, 2014.
PCT/US2015/066023, International Search Report and Written Opinion, dated Mar. 14, 2016.
PCT/US2015/066052, International Search Report and Written Opinion, dated Apr. 7, 2016.
Poghossian et al., "Functional testing and characterization of ISFETs on wafer level by means of a micro-droplet cell", *Sensors*, vol. 6, No. 4, Apr. 2006, 397-404.
Pollack et al., "Genome-wide analysis of DNA copy-number changes using cDNA microarrays", *Nature Genetics*, vol. 23, No. 1, Sep. 1999, 41-46.
Pourmand et al., "Direct electrical detection of DNA synthesis", *Proceedings of the National Academy of Sciences*, vol. 103, No. 17, Apr. 2006, 6466-6470.
Pouthas et al., "Spatially resolved electronic detection of biopolymers" *Physics Review*, vol.70, 3 Part 1, Sep. 2004, 031906-1 to 031906-8.
Premanode et al., "Ultra-low power precision ISFET readout using global current feedback", *Electronic Letters*, vol. 42, No. 22, Oct. 2006, 1264-1265.
Premanode et al., "A composite ISFED readout circuit employing current feedback", *Sensors and Actuators B: Chemical*, vol. 127, No. 2, Nov. 2007, 486-490.

(56) References Cited

OTHER PUBLICATIONS

Premanode et al., "A novel, low power biosensor for real time monitoring of creatine and urea in peritoneal dialysis", *Sensors and Actuators B: Chemical*, vol. 120, No. 2, Jan. 2007, 732-735.
Premanode et al., "Drift Reduction in Ion-Sensitive FETs using correlated double sampling", *Electronics Letters*, vol. 43, No. 16, Aug. 2, 2007, 857 (2 pages).
Purushothaman et al., Protons and single nucleotide polymorphism detection: A simple use for the Ion Sensitive Field Effect Transistor, *Sensors and Actuators B: Chemical*, vol. 114, No. 2, Apr. 2006, 964-968.
Purushothaman et al., "Towards Fast Solid State DNA Sequencing", *IEEE ISCAS 2002 Proceedings*, Circuits and Systems, vol. 4, 2002, IV-169 to IV-172.
Rodriguez-Villegas, "Solution to trapped charge in FGMOS transistors" *Electronics Letters*, vol. 39, No. 19, Nov. 20031416-1417.
Ronaghi et al., "A Sequencing Method Based on Real-Time Pyrophosphate", *Science*, vol. 281, 1998, 363-365.
Rothberg et al., "An integrated semiconductor device enabling non-optical genome sequencing", *Nature*, vol. 475, No. 7356, Jul. 21, 2011, 348-352.
Rowe et al., "An Array Immunosensor for Simultaneous Detection of Clinical Analytes", *Analytical Chemistry*, vol. 71, No. 2, 1999, pp. 433-439.
Sakata et al., "DNA Sequencing Based on Intrinsic Molecular Charges", *Angewandte Chemie International Edition*, vol. 45, 2006, 2225-2228.
Sakata et al., "Potentiometric Detection of DNA Using Genetic Transistor" *Denki Gakkai Kenkyukai Shiryo Chemical Sensor Kenkyukai*, CHS-03-51-55, 2003, 1-5.
Sakata et al., "Cell-based field effect devices fo cell adhesion analysis", *Intl. Conf. on Microtechnologies in Medicine and Biology*, Okinawa, Japan, 2006, 177-179.
Sakata et al., "Detection of DNA recognition events using multi-well field effect transistor", *Biosensors and Bioelectronics*, vol. 21, 2005, 827-832.
Sakata et al., "Detection sensitivity of genetic field effect transistor combined with charged nanoparticle-DNA conjugate", *Proc. of Intl. Conf. on Microtechnologies in Medicine and Biology*, May 9-12, 2005, Okinawa, Japan, 2006, 97-100.
Sakata et al., "Direct detection of single nucleotide polymorphism using genetic field effect transistor", *Digest of Papers Microprocesses and Nanotechnology*, Osaka, Japan, International Microprocesses and Nanotechnology Conference, 2004, 226-227.
Sakata et al., "Direct Detection of Single-Base Extension Reaction Using Genetic Field Effect Transistor", *Proc. of 3rd Ann. Intl. IEEE EMBS Special Topic Conf. on Microtechnologies in Medicine and Biology*, Kahuku, Oahu, HI, 12-15, 2005, 219-222.
Sakata et al., "Direct transduction of allele-specific primer extension into electrical signal using genetic field effect transistor", *Biosensors and Bioelectronics*, vol. 22, No. 7, Feb. 2007, 1311-1316.
Sakata et al., "DNA Analysis Chip Based on Field-Effect Transistors", *Japanese Journal of Applied Physics*, vol. 44, No. 4, Apr. 2005, 2854-2859.
Sakata et al., "DNA Sequencing Based on Intrinsic Molecular Charges", *Angewandte Chemie International Edition*, vol. 118, 2006, 2283-2286.
Sakata et al., "DNA Sequencing Using Genetic Field Effect Transistor", *13th Intl. Conf. on Solid-State Sensors, Actuators and Microsystems*, Jun. 5-9, 2005, Seoul, Korea, 1676-1679.
Sakata et al., "Immobilization of oligonucleotide probes on Si3N4 surface and its application to genetic field effect transistor", *Materials Science and Engineering: C*, vol. 24, 2004, 827-832.
Sakata et al., "Potential Behavior of Biochemically Modified Gold Electrode for Extended-Gate Field-Effect Transistor", *Japanese Journal of Applied Physics*, vol. 44, No. 4B, Apr. 2005, 2860-2863.
Sakata et al., "Potential Response of Genetic Field Effect Transistor to Charged Nanoparticle-DNA Conjugate", *Digest of Papers Microprocesses and Nanotechnology*, Tokyo, Japan, Intl Microprocesses and Nanotech Conference, Hotel Bellclassic, 2005, 42-43.

Sakata, T. et al., "Potentiometric Detection of Allele Specific Oligonucleotide Hybridization Using Genetic Field Effect Transistor", *Micro Total Analysis Systems*, 8th Intl. Conf. on Miniaturized Systems for Chemistry and Life Sciences, Sep. 26-30, 2004, Malmo, Sweden, 300-302.
Sakata et al., "Potentiometric Detection of DNA Molecules Hybridization Using Gene Field Effect Transistor and Intercalator", *Materials Research Society Symposium Proceedings*, vol. 782, Micro- and Nanosystems, Dec. 1-3, 2003, Boston, Massachusetts, 393-398.
Sakata et al., "Potentiometric Detection of Single Nucleotide Polymorphism by Using a Genetic Field-effect transistor", *ChemBioChem*, vol. 6, 2005, 703-710.
Sakurai et al., "Real-Time Monitoring of DNA Polymerase Reactions by a Micro ISFET pH Sensor", *Analytical Chemistry*, vol. 64, No. 1), 1992, 1996-1997.
Salama, "CMOS luminescence detection lab-on-chip: modeling, design, and characterization", *Thesis*, Presented at Stanford University, 2005, ii-78.
Salama, "Modeling and simulation of luminescence detection platforms", *Biosensors & Bioelectronics*, vol. 19, No. 11, Jun. 2004, 1377-1386.
Sawada et al., "A novel fused sensor for photo- and ion-sensing" *Sensors and Actuators B: Chemical*, vol. 106, No. 2, May 2005, 614-618.
Sawada et al., "Highly sensitive ion sensors using charge transfer technique", *Sensors and Actuators B: Chemical*, vol. 98, No. 1, Mar. 2004, 69-72.
Schasfoort et al., "A new approach to immunoFET operation", *Biosensors & Bioelectronics*, vol. 5, No. 2, 1990, 103-124.
Schasfoort et al., "Field-effect flow control for microfabricated fluidic networks", *Science*, vol. 286, No. 5441, Oct. 1999, 942-945.
Schoning et al., "Bio FEDs (Field-Effect Devices): State-of-the-Art and New Directions", *Electroanalysis*, vol. 18, Nos. 19-20, Oct. 2006, 1893-1900.
Schoning et al., "Recent advances in biologically sensitive field-effect transistors (BioFETs)", *Analyst*, vol. 127, No. 9, Sep. 2002, 1137-1151.
Schroder, "6. Oxide and Interface Trapped Charges, Oxide Thickness", *Semiconductor Material and Device Characterization, John Wiley & Sons*, ISBN: 978-0-471-73906-7, Feb. 17, 2006, 319-387.
Seong-Jin et al., "Label-Free CMOS DNA Quantification With On-Chip Noise Reduction Schemes", *Solid-State Sensors, Actuators and Microsystems Conference, IEEE*, Jun. 10, 2013, 947-950.
SG200903992-6, Search and Examination Report, dated Jan. 20, 2011.
Shah, "Microfabrication of a parellel-array DNA pyrosequencing chip", *NNIN REU Research Accomplishments*, 2005, 130-131.
Shepherd et al., "Towards Direct Biochemical Analysis with Weak Inversion ISFETS", *IEEE International Workshop on Biomedical Circuits & Systems*, 2004, S1.5-5 to S1.5.8.
Shepherd et al., "A biochemical translinear principle with weak inversion ISFETs", *IEEE Trans Circuits Syst—I*, vol. 52, No. 12, Dec. 2005, 2614-2619.
Shepherd et al., "A novel voltage-clamped CMOS ISFET sensor interface", *IEEE*, Jun. 25, 2007, 3331-3334.
Shepherd et al., "Weak inversion ISFETs for ultra-low power biochemical sensing and real-time analysis", *Sensors and Actuators B: Chemical*, vol. 107, No. 1, May 2005, 468-473.
Shi et al., "Radical Capillary Array Electrophoresis Microplace and Scanner for High-Performance Nucleic Acid Analysis", *Analytical Chemistry*, vol. 71, No. 23, Oct. 1999, 5354-5361.
Sia et al., "Microfluidic devices fabricated in poly(dimethylsiloxane) for biological studies", *Electrophoresis*, vol. 24, No. 21, Nov. 2003, 3563-3576.
Sibbald et al., "A miniature flow-through cell with a four-function ChemFET integrated circuit for simultaneous measurements of potassium, hydrogen, calcium and sodium ions", *Analytica Chimica Acta*, vol. 159, 1984, 47-62.
Simonian et al., "FET based biosensors for the direct detection of organophosphate neurotoxins", *Electroanalysis*, vol. 16, No. 22, Nov. 2004, 1896-1906.

(56) References Cited

OTHER PUBLICATIONS

Souteyrand et al., "Direct detection of the hybridization of synthetic homo-oligomer DNA sequences by field effect", *Journal of Physical Chemistry B*, vol. 101, No. 15, 1997, 2980-2985.
Starodub et al., "Immunosensor for the determination of the herbicide simazine based on an ion-selective field-effect transistor", *Analytica Chimica Acta*, vol. 424, No. 1, Nov. 2000, 37-43.
Takenaka et al., "DNA Sensing on a DNA Probe-Modified Electrode Using Ferrocenylnaphthalene Dimide as the Electrochemically Active Ligand", *Analytical Chemistry*, vol. 72, No. 6, Feb. 2000, 1334-1341.
Temes et al., "A Tutorial Discussion of the Oversampling Method for A/D and D/A Conversion", *IEEE International Symposium on Circuits and Systems*, vol. 2 of 4, 1990, 5 pages.
Terada et al., "Further Study of Vth-Mismatch Evaluation Circuit", *Proceedings of IEEE 2004 Int. Conference on Microelectronic Test Structures*, vol. 17, Mar. 22, 2004, 155-159.
Thewes et al., "CMOS-based Biosencor Arrays", *Proceedings of the Design, Automation and Test in Europe Conference and Exhibition*, 2005, 2 pages.
Tokuda et al., "A CMOS image sensor with optical and potential dual imaging function for on-chip bioscientific applications", *Sensors and Actuators A: Physical*, vol. 125, No. 2, Jan. 2006, 273-280.
Tomaszewski et al., "Electrical characterization of ISFETs" *Journal of Telecommunications ad Information Technology*, Mar. 2007, 55-60.
Toumazou et al., "Using transistors to linearase biochemistry", *Electronics Letters*, vol. 43, No. 2, Jan. 18, 2007, 3 pages.
Truman, "Monitoring liquid transport and chemical composition in lab on . . . ", *Lab on a Chip*, vol. 6, No. 9, Jul. 2006, 1220-1228.
Unger et al., "Monolithic Microfabricated Valves and Pumps by Multilayer Soft Lithography", *Science*, vol. 288, No. 5463, Apr. 2000, 113-116.
Uslu et al., "Labelfree fully electronic nucleic acid detection system based on a field-effect transistor device", *Biosensors & Bioelectronics*, vol. 19, No. 12, 2004, 1723-1731.
Van Der Schoot et al., "The Use of a Multi-ISFET Sensor Fabricated in a Single Substrate", *Sensors and Actuators*, vol. 12, No. 4, Nov. 1987, 463-468.
Van Der Wouden et al., "Directional flow induced by synchronized longitudinal and zeta-potential controlling AC-electrical fields", *Lab Chip*, vol. 6, No. 10, Oct. 2006, 1300-1305.
Van Hal et al., "A general model to describe the electrostatic potential at electrolyte oxide interfaces", *Advances in Colloid and Interface Science*, vol. 69, 1996, 31-62.
Van Kerkhof, "The Development of an ISFET based heparin sensor using the ion-step measuring method", *Biosensors and Bioelectronics*, vol. 9, Nos. 9-10, 1993, 463-472.
Van Kerkhof, The Development of an ISFET-based Heparin Sensor, *Thesis*, 1994.
Van Kerkhof et al., "The ISFET based heparin sensor with a monolayer of protamine as affinity ligand", *Biosensors & Bioelectronics*, vol. 10, No. 3, 1995, 269-282.
Van Kerkhof, J. et al., "ISFET Responses on a stepwise change in electrolyte concentration at constant pH", *Sensors Actuators B: Chemical*, vol. 18-19, 1994, 56-59.
Vardalas, "Twists and Turns in the Development of the Transistor", *IEEE-USA Today's Engineer Online*, May 2003, 6 pages.
Voigt et al., "Diamond-like carbon-gate pH-ISFET", *Sensors and Actuators B: Chemical*, vol. 44, 1997, 441-445.
Wagner et al., "'All-in-one' solid-state device based on a light-addressable potentiometric sensor platform", *Sensors and Actuators B: Chemical*, vol. 117, 2006, 472-479.
Wang et al., "Label-free detection of small-molecule-protein interactions by using nanowire nanosensors", *Proceedings of the National Academy of Sciences*, vol. 102, No. 9, 2005, 3208-3212.
Wen-Yaw et al., "New ISFET interface circuit design with tempreature Compensation", *CiteSeerx*—URL: http://citeseerx.ist.psu.edu/viewdoc/download?doi=10.1.1.95.2321&rep=rep1&type=pdf, 2006, 1.
Wilhelm et al., "pH Sensor Based on Differential Measurements on One pH-FET Chip", *Sensors and Actuators B: Chemical*, vol. 4, 1991, 145-149.
Woias, "Modelling the short time response of ISFET sensors", *Sensors and Actuators B*, vol. 24- 25, 1995, 211-217.
Woias et al., "Slow pH response effects of silicon nitride ISFET sensors" *Sensors and Actuators B: Chemical*, vol. 48, 1998, 501-504.
Wood et al., "Base composition-independent hybridization in tetramethylammonium chloride: a method for oligonucleotide screening of highly complex gene libraries", *Proceedings of the National Academy of Sciences*, vol. 82, 1985, 1585-1588.
Wu et al., "DNA and protein microarray printing on silicon nitride waveguide surfaces", *Biosensens & Bioelectronics*, vol. 21, No. 7, 2006, 1252-1263.
Xu et al., "Analytical Aspects of FET-Based Biosensors", *Frontiers in Bioscience*, vol. 10, 2005, 420-430.
Yeow et al., "A very large integrated pH-ISFET sensor array chip compatible with standard CMOS processes", *Sensor and Actuators B: Chemical*, vol. 44, 1997, 434-440.
Yoshida et al., "Development of a Wide Range pH Sensor based on Electrolyte-Insulator-Semiconductor Structure with Corrosion-Resistant Al2O3—Ta2O5 and Al2O3—ZrO2", *Journal of the Electrochemical Society vol. 151*, No. 3, 2004, H53-H58.
Yuqing et al., "Ion sensitive field effect transducer-based biosensors", *Biotechnology Advances*, vol. 21, 2003, 527-534.
Zhang et al., "32-Channel Full Customized CMOS Biosensor Chip for Extracellular neural Signal Recording", *Proc. of the 2nd Intl. IEEE EMBs Conf. on Neural Engineering*, Arlington, Virginia, 2005, v-viii.
Zhao et al., "Floating-Gate Ion Sensitive Field-Effect Transistor for Chemical and Biological Sensing", *MRS Proceeding*, vol. 828, 2005, 349-354.
Zhou et al., "Quantitative detection of single nucleotide polymorphisms for a pooled sample by a bioluminometric assay coupled with modified primer extension reactions (BAMPER)", *Nuc. Acids Res.*, vol. 29, No. 19, e93, 2001, 1-11.

\* cited by examiner

ION-SENSING CHARGE-ACCUMULATION CIRCUITS AND METHODS

RELATED APPLICATIONS

This application is a continuation of U.S. application Ser. No. 14/964,938 filed Dec. 10, 2015, which is a U.S. application Ser. No. 14/477,125 filed Sep. 4, 2014 (now U.S. Pat. No. 9,239,313), which is a continuation of U.S. application Ser. No. 13/173,146 filed Jun. 30, 2011 (now U.S. Pat. No. 8,858,782), which claims the benefit of U.S. Provisional Application No. 61/360,493 filed Jun. 30, 2010; 61/360,495 filed Jul. 1, 2010; and 61/361,403, filed Jul. 3, 2010; each of which is herein incorporated by reference in their entirety.

BACKGROUND

Electronic devices and components have found numerous applications in chemistry and biology (more generally, "life sciences"), especially for detection and measurement of various chemical and biological reactions and identification, detection and measurement of various compounds. One such electronic device is referred to as an ion-sensitive field effect transistor, often denoted in the relevant literature as an "ISFET" (or pHFET). ISFETs conventionally have been explored, primarily in the academic and research community, to facilitate measurement of the hydrogen ion concentration of a solution (commonly denoted as "pH"). The chemically-sensitive sensor referred to herein may be implemented using an ISFET, phFET, chemFet or some other transistor device capable of performing a similar function.

More specifically, an ISFET is an impedance transformation device that operates in a manner similar to that of a MOSFET (Metal Oxide Semiconductor Field Effect Transistor), and is particularly configured to selectively measure ion activity in a solution (e.g., hydrogen ions in the solution are the "analytes"). A detailed theory of operation of an ISFET is given in "Thirty years of ISFETOLOGY: what happened in the past 30 years and what may happen in the next 30 years," P. Bergveld, Sens. Actuators, 88 (2003), pp. 1-20 ("Bergveld"), which publication is hereby incorporated herein by reference in its entirety.

Details of fabricating an ISFET using a conventional CMOS (Complementary Metal Oxide Semiconductor) process may be found in Rothberg, et al., U.S. Patent Publication No. 2010/0301398, Rothberg, et al., U.S. Patent Publication No. 2010/0282617, and Rothberg et al, U.S. Patent Publication 2009/0026082; these patent publications are collectively referred to as "Rothberg", and are all incorporated herein by reference in their entirety. In addition to CMOS, however, biCMOS (i.e., bipolar and CMOS) processing may also be used, such as a process that would include a PMOS FET array with bipolar structures on the periphery. Alternatively, other technologies may be employed wherein a sensing element can be made with a three-terminal devices in which a sensed ion leads to the development of a signal that controls one of the three terminals; such technologies may also include, for example, GaAs and carbon nanotube technologies.

Taking a CMOS example, a P-type ISFET fabrication is based on a p-type silicon substrate, in which an n-type well forming a transistor "body" is formed. Highly doped p-type (p+) regions S and D, constituting a source and a drain of the ISFET, are formed within the n-type well. A highly doped n-type (n+) region B may also be formed within the n-type well to provide a conductive body (or "bulk") connection to the n-type well. An oxide layer may be disposed above the source, drain and body connection regions, through which openings are made to provide electrical connections (via electrical conductors) to these regions. A polysilicon gate may be formed above the oxide layer at a location above a region of the n-type well, between the source and the drain. Because it is disposed between the polysilicon gate and the transistor body (i.e., the n-type well), the oxide layer often is referred to as the "gate oxide."

Like a MOSFET, the operation of an ISFET is based on the modulation of charge concentration (and thus channel conductance) caused by a MOS (Metal-Oxide-Semiconductor) capacitance. This capacitance is constituted by a polysilicon gate, a gate oxide and a region of the well (e.g., n-type well) between the source and the drain. When a negative voltage is applied across the gate and source regions, a channel is created at the interface of the region and the gate oxide by depleting this area of electrons. For an n-well, the channel would be a p-channel (and vice-versa). In the case of an n-well, the p-channel would extend between the source and the drain, and electric current is conducted through the p-channel when the gate-source potential is negative enough to attract holes from the source into the channel. The gate-source potential at which the channel begins to conduct current is referred to as the transistor's threshold voltage VTH (the transistor conducts when VGS has an absolute value greater than the threshold voltage VTH). The source is so named because it is the source of the charge carriers (holes for a p-channel) that flow through the channel; similarly, the drain is where the charge carriers leave the channel.

As described in Rothberg, an ISFET may be fabricated with a floating gate structure, formed by coupling a polysilicon gate to multiple metal layers disposed within one or more additional oxide layers disposed above the gate oxide. The floating gate structure is so named because it is electrically isolated from other conductors associated with the ISFET; namely, it is sandwiched between the gate oxide and a passivation layer that is disposed over a metal layer (e.g., top metal layer) of the floating gage.

As further described in Rothberg, the ISFET passivation layer constitutes an ion-sensitive membrane that gives rise to the ion-sensitivity of the device. The presence of analytes such as ions in an analyte solution (i.e., a solution containing analytes (including ions) of interest or being tested for the presence of analytes of interest), in contact with the passivation layer, particularly in a sensitive area that may lie above the floating gate structure, alters the electrical characteristics of the ISFET so as to modulate a current flowing through the channel between the source and the drain of the ISFET. The passivation layer may comprise any one of a variety of different materials to facilitate sensitivity to particular ions; for example, passivation layers comprising silicon nitride or silicon oxynitride, as well as metal oxides such as silicon, aluminum or tantalum oxides, generally provide sensitivity to hydrogen ion concentration (pH) in an analyte solution, whereas passivation layers comprising polyvinyl chloride containing valinomycin provide sensitivity to potassium ion concentration in an analyte solution. Materials suitable for passivation layers and sensitive to other ions such as sodium, silver, iron, bromine, iodine, calcium, and nitrate, for example, are known, and passivation layers may comprise various materials (e.g., metal oxides, metal nitrides, metal oxynitrides). Regarding the chemical reactions at the analyte solution/passivation layer interface, the surface of a given material employed for the passivation layer of the ISFET may include chemical groups that may donate protons to or accept protons from the analyte solution, leaving at any given time negatively charged, positively charged, and neutral sites on the surface of the passivation layer at the interface with the analyte solution.

With respect to ion sensitivity, an electric potential difference, commonly referred to as a "surface potential," arises at the solid/liquid interface of the passivation layer and the analyte solution as a function of the ion concentration in the sensitive area due to a chemical reaction (e.g., usually involving the dissociation of oxide surface groups by the ions in the analyte solution in proximity to the sensitive area). This surface potential in turn affects the threshold voltage of the ISFET; thus, it is the threshold voltage of the ISFET that varies with changes in ion concentration in the analyte solution in proximity to the sensitive area. As described in Rothberg, since the threshold voltage VTH of the ISFET is sensitive to ion concentration, the source voltage VS provides a signal that is directly related to the ion concentration in the analyte solution in proximity to the sensitive area of the ISFET.

Arrays of chemically-sensitive FETs ("chemFETs"), or more specifically ISFETs, may be used for monitoring reactions—including, for example, nucleic acid (e.g., DNA) sequencing reactions, based on monitoring analytes present, generated or used during a reaction. More generally, arrays including large arrays of chemFETs may be employed to detect and measure static and/or dynamic amounts or concentrations of a variety of analytes (e.g., hydrogen ions, other ions, non-ionic molecules or compounds, etc.) in a variety of chemical and/or biological processes (e.g., biological or chemical reactions, cell or tissue cultures or monitoring, neural activity, nucleic acid sequencing, etc.) in which valuable information may be obtained based on such analyte measurements. Such chemFET arrays may be employed in methods that detect analytes and/or methods that monitor biological or chemical processes via changes in charge at the chemFET surface. Such use of ChemFET (or ISFET) arrays involves detection of analytes in solution and/or detection of change in charge bound to the chemFET surface (e.g. ISFET passivation layer).

Research concerning ISFET array fabrication is reported in the publications "A large transistor-based sensor array chip for direct extracellular imaging," M. J. Milgrew, M. O. Riehle, and D. R. S. Cumming, Sensors and Actuators, B: Chemical, 111-112, (2005), pp. 347-353, and "The development of scalable sensor arrays using standard CMOS technology," M. J. Milgrew, P. A. Hammond, and D. R. S. Cumming, Sensors and Actuators, B: Chemical, 103, (2004), pp. 37-42, which publications are incorporated herein by reference and collectively referred to hereafter as "Milgrew et al." Descriptions of fabricating and using ChemFET or ISFET arrays for chemical detection, including detection of ions in connection with DNA sequencing, are contained in Rothberg. More specifically, Rothberg describes using a chemFET array (in particular ISFETs) for sequencing a nucleic acid involving incorporating known nucleotides into a plurality of identical nucleic acids in a reaction chamber in contact with or capacitively coupled to chemFET, wherein the nucleic acids are bound to a single bead in the reaction chamber, and detecting a signal at the chemFET, wherein detection of the signal indicates release of one or more hydrogen ions resulting from incorporation of the known nucleotide triphosphate into the synthesized nucleic acid.

FIG. 1 is a cross-sectional diagram depicting an embodiment of a physical structure of an ion-sensing system 20 that can include an ISFET 24, a solution 28 provided at an ion-sensitive surface 32 of the ISFET 24, and an electrode 36 in the solution 28 providing a reference voltage VREFA. The ISFET 24 can be fabricated in a CMOS process, and include n-type source and drain diffusion regions 40, 44 formed in a p-type silicon substrate 48, source and drain connections 52, 56, a gate oxide layer 60 over a channel-forming region 64 between the source and drain 40, 44, a floating gate structure 68 formed over the gate oxide 60, and a passivation layer 72 formed over the gate structure 68. The floating gate structure 68 can include a polysilicon gate 78 and one or more metal layers 76 and via interconnections 80. The source and drain connections 52, 54 can also include one or more metal layers 76 and via interconnections 80. A dielectric isolation 84 can separate these various structures.

In operation, the reference voltage VREFA can be supplied to the electrode 36 in the solution 28, and the source and drains 40, 44 of the ISFET 24 can be electrically connected to readout circuitry (not shown) through the source and drain connection structures 52, 56. The gate 78 of the ISFET 24 may have no direct electrical connection to other circuits, and thus can be an electrically floating structure. The effect of the ion concentration on the operation of the ISFET 24 can be modeled as a dependence of a threshold voltage of the ISFET 24 on the ion concentration in the solution 28 resulting from an electrochemical interaction between the ion-sensitive passivation surface 32 of the ISFET 24 and ions in the adjacent solution 28. The ion-sensing system 20 can thus determine the ion concentration from a threshold voltage change, itself determined by measuring a current or voltage change at the source or drain 40, 44 of the ISFET 24, given a known reference voltage VREFA and readout circuit type and operation.

However, problems exist with the ion-sensing system 20 of FIG. 1 and its use to detect the ion concentration of the solution 28. The change to the voltage or current at the source or drain 40,44 of the ISFET 24, and thus in the readout circuit, induced by the change in threshold voltage can be small and difficult to accurately measure. Additionally, the threshold voltage itself can be a non-linear function of other variables, such as the voltage across the source 40 to the substrate 48 (i.e., body) of the ISFET 24. This can limit the linearity of the threshold voltage calculations, if the source-to-body voltage is allowed to vary, or limit the type of readout circuit that can be used, if the source-to-body voltage is to be maintained relatively constant to preserve linearity. In a similar vein, both dynamic range and signal-to-noise performance of the ion-sensing system 20 of FIG. 1 are concerns. Overall, these concerns can necessitate the use of complex, and thus space-consuming and costly, readout circuits, or limit the performance metrics that can be achieved using this ion-sensing system 20.

Thus, a need exists for a way to achieve improved speed, accuracy, linearity and other performance metrics when measuring ion concentration in a solution, but while still utilizing devices that can be manufactured in bulk using a CMOS process.

BRIEF DESCRIPTION OF THE DRAWINGS

So that features of the present invention can be understood, a number of drawings are described below. However, the appended drawings illustrate only particular embodiments of the invention and are therefore not to be considered limiting of its scope, for the invention may encompass other equally effective embodiments.

DETAILED DESCRIPTION

An ion-sensitive circuit can include a charge accumulation device, to accumulate a plurality of charge packets as a function of an ion concentration of a fluid, and at least one control and readout transistor, to generate an output signal as a function of the accumulated plurality of charge packets, the output signal representing the ion concentration of the solution. The charge accumulation device can include a first charge control electrode above a first electrode semiconductor region, an electrically floating gate structure above a gate semiconductor region and below an ion-sensitive passivation surface, a second charge control electrode above a second electrode semiconductor region, and a drain diffusion region. The first control electrode can control entry of charge into a gate semiconductor region in response to a first control signal. The ion-sensitive passivation surface can be configured to receive the fluid. The second charge control electrode can control transmission of the plurality of charge packets out of the gate semiconductor region and into the drain diffusion region in response to a second control signal. The drain diffusion region can receive the plurality of charge packets from the gate semiconductor region via the second electrode semiconductor region.

The ion-sensitive circuit can operate according to a method to detect the ion concentration of the fluid. The method can include (i) passing the fluid having the ion concentration over the ion-sensitive passivation surface of the charge accumulation device; (ii) individually forming, one at a time, the plurality of charge packets in the gate semiconductor region of the charge accumulation device as a function of the ion concentration in the fluid; (iii) applying a control signal to the second control electrode of the charge accumulation device to control transmission of the charge packets one at a time from the gate semiconductor region; (iv) accumulating the plurality of charge packets at the drain diffusion region of the charge accumulation device at a selectable charge packet accumulation frequency; and (v) generating an output signal using the at least one control and readout transistor as a function of the accumulated plurality of charge packets at the drain region at a selectable output signal generation frequency, wherein the output signal represents a measure of the ion concentration in the fluid.

Figure 2:
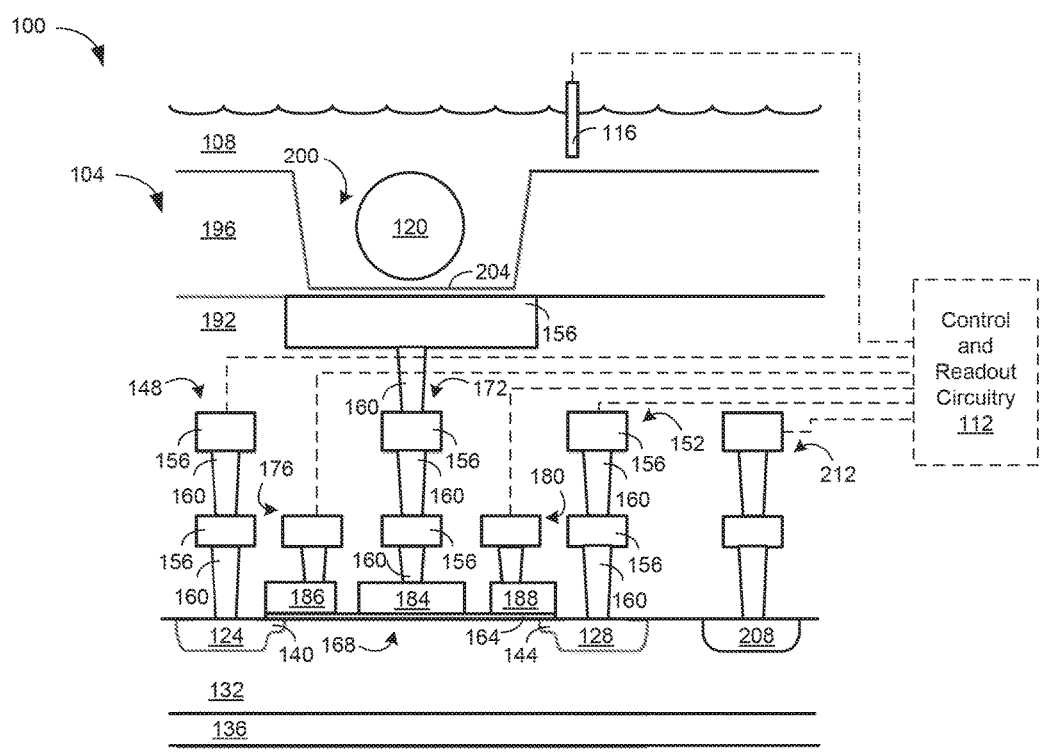
FIG. 2 is a partially cross-sectional, partially schematic diagram of an ion-sensing system including a ion-sensitive charge accumulation device.

FIG. 2 depicts a partially cross-sectional, partially schematic view of an embodiment of an ion-sensing system 100, having an ion-sensitive charge-accumulation device 104, that can detect ion concentration in a solution 108 to perform DNA sequencing and other applications. The ion sensing system 100 can include the charge-accumulation device 104, a control and readout circuit 112, an electrode 116, the solution 108 and a micro-particle or micro-bead 120. In FIG. 2, the charge-accumulation device 104, electrode 116, solution 108 and micro-particle 120 are depicted in a cross-sectional representation, while the control circuit 112, and its connection to terminals of the charge-accumulation device 104 are depicted schematically. For convenience, the schematic portions of FIG. 2 are indicated by dashed lines.

The charge accumulation device 104 can be fabricated in a CMOS process and be part of an integrated circuit including the charge-accumulation device 104 and the control and readout circuit 112. N-type source and drain diffusion regions 124, 128 can be formed in a p-type epitaxial layer 132 formed on a p-type silicon substrate 136. The source and drain diffusion regions 124, 128 can have lightly-doped portions 140, 144 with relatively less doping than other portions of the drain and diffusion regions 124, 128. Source and drain connections 148, 152 can include one or more metal layers 156 and via interconnections 160. A gate oxide layer 164 can be formed over a region 168 of the p-type epitaxial layer 132 between the source and drain 124, 128, and a floating gate structure 172 and first and second control electrode structures 176, 180 can formed over the gate oxide 164. The gate oxide 164 can include a material such as silicon dioxide. The floating gate structure 172 can include a n-type polysilicon gate 184 and one or more metal layers 156 and via interconnections 160. The control electrode structures 176, 180 can also include first and second n-type polysilicon electrodes 186, 188, respectively, and one or more metal layers 156 and via interconnections 160. The metal layers 156 and vias 160 can each include one or more layers of conductive materials such as tungsten, aluminum, copper, titanium, and nitrides and silicides thereof. Dielectric isolation 192 between these various structures can include one or more layer of silicon oxide, borophosphosilicate glass, or combinations thereof. A passivation layer 196 can be formed over the gate structure 172 and dielectric isolation 196, and include a well 200 having an ion-sensitive surface 204 to accommodate the micro-particle 120 (or micro-bead 120), which can have a plurality of replicated DNA strands attached to its surface. The passivation layer 196 can include a material such as silicon nitride, silicon oxynitride, and polyimide. A substrate connection diffusion region 208 and can have an associated connection structure 212 similar to the drain and source connection structures 148, 152.

Reference to diffusion regions 124, 128 as source and drain diffusion regions 124, 128 is for convenience of reference herein. These diffusion regions 124, 128, however, do not need to have all the same properties as a source and drain of a transistor. Instead, the source and drain diffusion regions 124, 128 can also be referred to as simply diffusion regions 124, 128, without necessarily implying transistor source and drain functionality. In some instances, however, as is apparent from the description herein, the diffusion regions 124, 128 may indeed have properties like those of a source and drain of a transistor.

The ion-sensing system 100 can be used to perform DNA sequencing or other applications involving the sensing of ions in the solution 108. A plurality of the DNA-strand-bearing micro-particles 120 can be introduced to a surface of an integrated circuit containing a plurality of the charge-accumulation devices 104 depicted in FIG. 2, with the micro-particles 120 settling into the wells 200 of the passivation layer 196. A plurality of different solutions 108 can be sequentially introduced to and received by the surface of the integrated circuit, including in the wells 200 in the passivation layer 196. Each of the solutions 108 in the sequential series of solutions can include a different nucleotide or nucleobase. Each solution, or reagent, may or may not react with the DNA strands attached to the micro-particle 120, depending on whether the solution's particular nucleotide or nucleobase matches or compliments a currently reactive position along the sequence of nucleobases of the attached DNA strands. When a particular solution 108 in the sequence of administered solutions does react with the DNA strands, a plurality of ions, such as, e.g., protons (e.g., hydrogen H+ ions), pyrophosphate (i.e., PPi), or both, may be released. The ion-sensitive charge-accumulation device 104 can detect the concentration of ions in the solution 108, according to principles of its operation discussed herein, to provide data as to the identity of the nucleobase of the currently reactive position of the attached DNA strands, thereby providing data to sequence the strands.

In operation, the ion-sensitive charge-accumulation device 104 can generate and accumulate a plurality of charge packets 216 (shown, e.g., in FIGS. 3A-3D) as a function of and in response to ion concentrations in the solution 108 provided to the ion-sensitive surface 204 of the well 200 in the passivation layer 196, using potential energy barriers and gradients created through the application of control signals to the source 124, drain 128, first and second control electrodes 186, 188 by the control and readout circuitry 112. FIGS. 3A-D depict embodiments of a plurality of cycles of operation of the charge-accumulation device 104 to generate and accumulate charge packets in response to ion concentrations in the solution 108. Each of FIGS. 3A-3D can depict a complete cycle of an embodiment of operation of the charge accumulation device 104. The top of each of FIGS. 3A-3D depicts a simplified partially cross-sectional, partially schematic representation of the charge-accumulation device 104, showing only the source and drain regions 124, 128, the gate oxide 164, the floating gate 184, and the first and second control electrodes 186, 188. For convenience of illustration and explanation, other components of the charge-accumulation device 104 are omitted from the depictions, although omitted components can be present in actual embodiments. In each figure, below the representation of the charge-accumulation device 14 are four diagrams depicting potential energies and charge present in the charge accumulation device 104 at different stages during the operational cycle of the device 104. Each of these diagrams is aligned to and depicts the potential energy and charge in specific spatial regions of the charge accumulation device 104 depicted at the top of the figure, so that each diagram therefore depicts the potential energy and charge in the n-type source and drain regions 124, 128 and in the p-type epitaxial regions under the control electrodes 186, 188 and the floating gate 184.

Figures 3A, 3B, 3C, 3D:
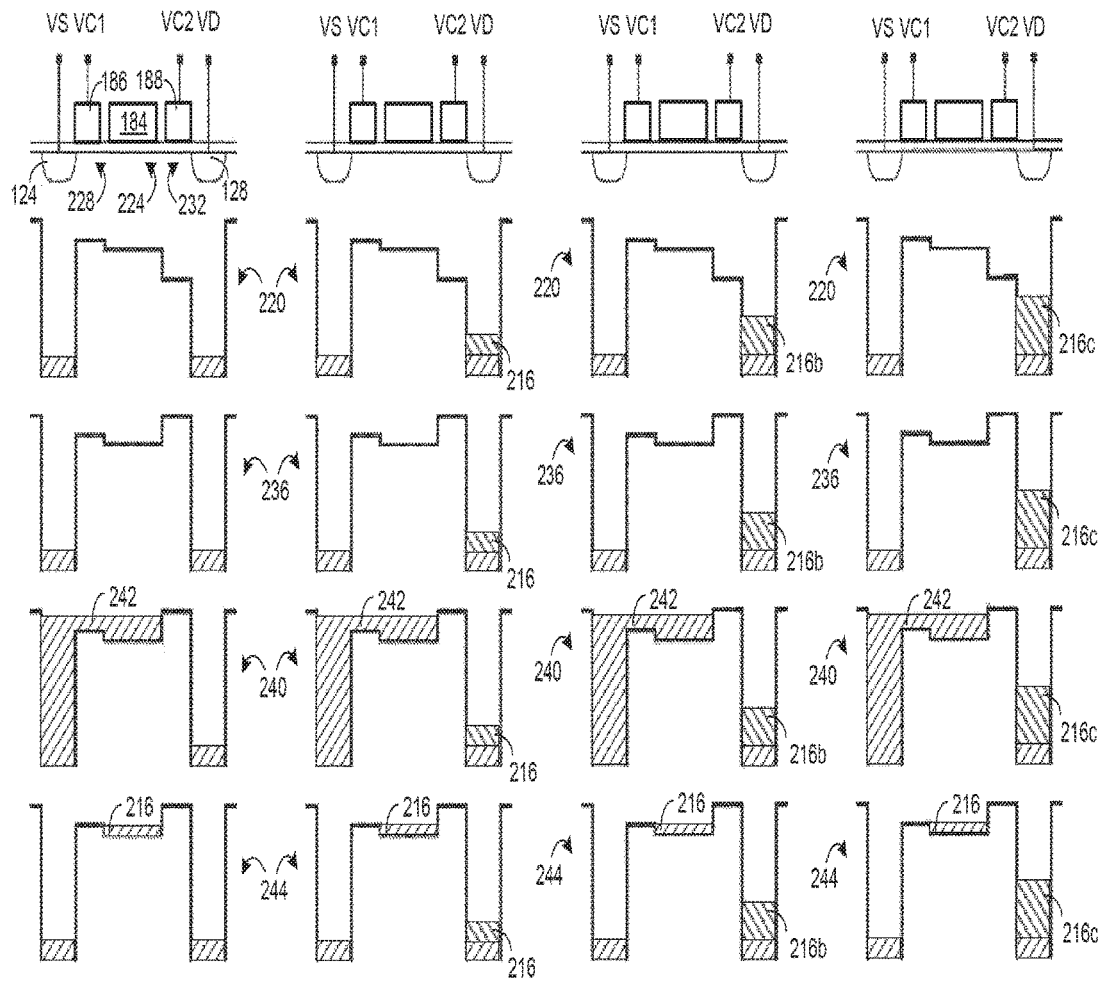
FIGS. 3A-3D are cross-sectional, potential and charge diagrams depicting an embodiment of an operational cycle of the ion-sensitive charge accumulation device.
Figure 4:
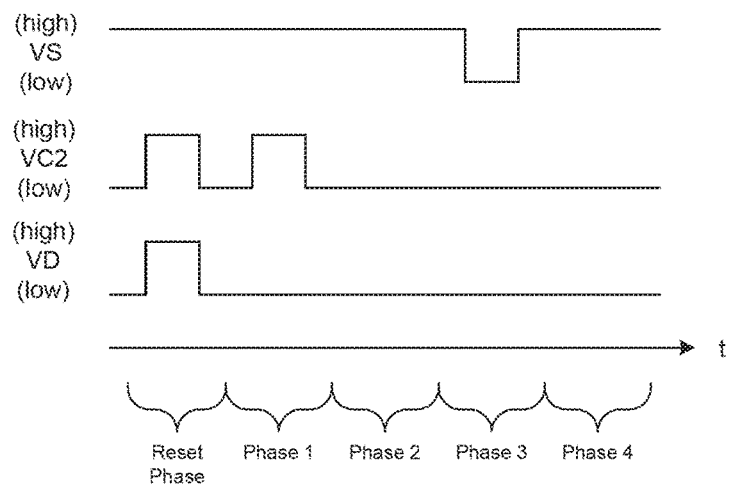
FIG. 4 is a signal diagram depicting an embodiment of control signals for controlling the operation of the charge accumulation device.

FIG. 4 is a signal diagram depicting an embodiment of a plurality of control signals that can be used to control the operation of the charge accumulation device 104 depicted in FIGS. 3A-3D. In FIG. 4, control signals VS, VD, VC2 delivered to the source 124, drain 128 and second control electrode 188 can vary between voltage values representing logic low and logic high states, such as lower and upper power supply voltages. Another control signal VC1 (not shown) can be delivered to the first control electrode 186, and may not represent a logic state and instead may assume an intermediate voltage value, such as a value between lower and upper power supply voltages. Other embodiments of control signals are possible, such as various combinations of control signals that vary between voltage values representing logic low and logic high states (such as lower and upper power supply voltages) and control signals that do not represent logic states and instead assume intermediate voltage values (such as a value between lower and upper power supply voltages). Embodiments of control signals can also be a function of specific embodiments of the physical structure of the charge-accumulation device 104. For example, the height of the gate oxide 164 between the first control electrode 186, floating gate 184, and second control electrode 188 can be selected to control the relative impact on potential energy in the charge accumulation device 104 of a given control voltage delivered to the first control electrode 186, floating gate 184 and second control electrode 188, respectively.

Prior to a first phase of the operational cycle depicted in FIG. 3A, in a pre-cycle reset phase (not shown in FIG. 3A), any charge remaining in the charge accumulation device 104 from a previous operation of the device 104 can be removed by delivering suitable control signals to the source 124, drain 128 and control electrodes 186, 188. In the embodiment depicted in FIG. 4, a high voltage can be delivered to the drain 124 and second control electrode 188, a low voltage to the source 124, and an intermediate voltage to the first control electrode 186 to clear any charge from a previous operation of the device 104.

In a first phase 220 of the operational cycle depicted in FIG. 3A, any charge packet 216 formed in the semiconductor region 224, e.g., p-type epitaxial region 224, under the floating gate 184 can be transferred to the drain diffusion region 208. This can be done by creating a potential gradient in the semiconductor regions 228, 224, 232 under the first control electrode 186, gate 184, and second control electrode 188 to direct the charge under the gate 184 to move to the drain diffusion region 208. Specifically, a relatively lower potential, and thus a relatively higher barrier to electron flow, can be created in the region 228 under the first control electrode 186, and a relatively higher potential, and thus a relatively lower barrier to electron flow, can be created in the region 232 under the second control electrode 188.

The potential diagrams of FIGS. 3A-3D, and other potential diagrams depicted and discussed herein, follow the convention that increasing potential energies correspond to downward directions in the potential energy diagrams. Thus, relatively higher potential energies are depicted by spatially lower indications in the diagrams. Relatively higher potential energies can be induced in p-type regions by applying relatively higher voltages to the control electrodes 186, 188 or such manifesting on the floating gate 184, and can represent a lower potential barrier to the accumulation or passage of electrons in p-type regions. By contrast, relatively lower potential energies can be induced in p-type regions by relatively lower voltages applied to the control electrodes 186, 188 or such manifesting on the floating gate 184, and can represent a higher potential barrier to the accumulation or passage of electrons in p-type regions.

Returning to FIG. 3A, the first stage potential energy gradient can be created in the regions 228, 224, 232 under the first control electrode 186, floating gate 184 and second control electrode 188 by application or manifestation of increasing voltages to the first control electrode 186, floating gate 184 and second control electrode 188, respectively, assuming a uniform gate oxide thickness. Alternatively, this potential energy gradient can also be created with other applied or manifested voltages and a non-uniform gate oxide thickness. FIG. 4 depicts an embodiment in which a high voltage can be delivered to the second control electrode 188 and source 124, a low voltage can be delivered to the drain 124, and the intermediate voltage to the first control electrode 186 in the first phase. Other embodiments of first phase control signals are possible.

Note that, because FIG. 3A depicts the first of several cycles of operation of the charge accumulation device 104 after a pre-cycle reset phase has removed any remaining charge packets 216 from a previous operation, no charge packet 216 has yet developed under the gate 184, and thus no charge packet 216 is transferred to the drain 128 in the first phase 220 depicted in FIG. 3A. However, the transfer during the first phase 220 of the charge packet 216 from under the gate 184 to the drain region 128 can be illustrated by the succeeding cycles depicted in FIGS. 3B-3D.

In a second phase 236 of the operational cycle depicted in FIG. 3A, the potential barrier under the second control electrode 188 can be raised to prevent charge packet flow from the region 224 under the gate 184 through the region 232 under the second electrode 188 to the drain region 128. FIG. 4 depicts an embodiment of second phase control signals in which a low voltage can be delivered to the second control electrode 188 and drain 128, a high voltage to the source 124, and the intermediate voltage to the first control electrode 186. Other second phase control signal embodiments are possible.

In a third phase 240 of the operational cycle depicted in FIG. 3A, charge, e.g., electrons, can be injected into the p-type region 224 under the floating gate 184 from the n-type source region 124. Because the potential barrier under the second electrode 188 has been raised during the second phase 236 to be higher than under the first control electrode 186 and floating gate 184, the charge 242 can flood the charge accumulation device 104 from the source 124 to under the first control electrode 186 and the floating gate 184, but not under the second control electrode 188. Charge 242 can be injected into the charge accumulation device 104 through the source 124 in various ways, such as through the use of a current source or charge pump selectively injecting charge into the source 124, or by applying a suitable voltage to the source 124 in the context of voltages supplied to or manifesting elsewhere in the charge accumulation device 104, e.g., on the first control electrode 186 and floating gate 184. FIG. 4 depicts an embodiment of the control signals in which a low voltage can be delivered to the source 124, while relatively higher voltages can be delivered or manifest on the first control electrode 186 and floating gate 184 (e.g., the intermediate voltage delivered to the first control electrode 186 and the potential induced on the floating gate 184 by the ion concentration in the solution 108).

In a fourth phase 244, the charge injection from the source 124 into the charge accumulation device 104 can be ended, and excess charge in the source 124 and under the first control electrode 186 withdrawn. However, because a potential differential can exist between under the first control electrode 186 and under the floating gate 184, a packet of charge 216 can remain under the floating gate 184 as a result of this potential difference. This potential difference can be a function of the voltage VC1 applied to the first control electrode 186 and the voltage manifesting on the floating gate 184 due to the ion concentration in the solution 104. Thus, the size of the charge packet 216 remaining under the floating gate 184 in the fourth phase 244 can be a function of the voltage VC1 applied to the first control electrode 186 and the voltage manifesting on the floating gate 184 due to the ion concentration in the solution 108, and thus a measure of the ion concentration in the solution 108, given a known voltage VC1 applied to the first control electrode 186.

Finally, in a first phase 220 of the next cycle of operation of the charge accumulation device 104, depicted in FIG. 3B, and as discussed above in regard to the first phase 220 of the first cycle of operation depicted in FIG. 3A, the charge packet 216 remaining under the floating gate 184 after the fourth stage 244 of the first cycle of operation can be transferred from under the gate 184, through the region 232 under the second control electrode 188, and into the drain diffusion region 128, where it can be maintained. Thus, after a single cycle of operation, a single charge packet 216, having a size that can be a measure of the ion concentration of the solution 108, can have been collected at the drain 128 of the charge accumulation device 104.

Although the charge accumulation device 104 can provide a measure of the ion concentration in the solution 104 with just a single charge packet 216 collected at the drain 128, the charge accumulation device 104 can also detect and provide a measure of the ion concentration in the solution 108 by collecting a plurality of charge packets 216 at the drain 128 over a plurality of cycles of operation of the charge accumulation device 104. The collected plurality of charge packets 216 can also provide a measure of the ion concentration in the solution 108. FIGS. 3B-3D depict second, third and fourth cycles of operation of the charge accumulation device 104 following the first cycle of operation depicted in FIG. 3A. After each cycle, another charge packet 216 can be accumulated at the drain 128 as a function of the ion concentration. In FIG. 3B, in a first phase 220 of the second cycle, a first charge packet 216 can be trapped at the drain 128 after the first cycle depicted in FIG. 3A. In FIG. 3C, in a first phase 220 of the third cycle, first and second charge packets 216b can be accumulated at the drain 128 following the second cycle depicted in FIG. 3B. In FIG. 3D, in a first phase 220 of the fourth cycle, first, second and third charge packets 216c can be accumulated at the drain 128 following the third cycle depicted in FIG. 3C.

Figure 1:
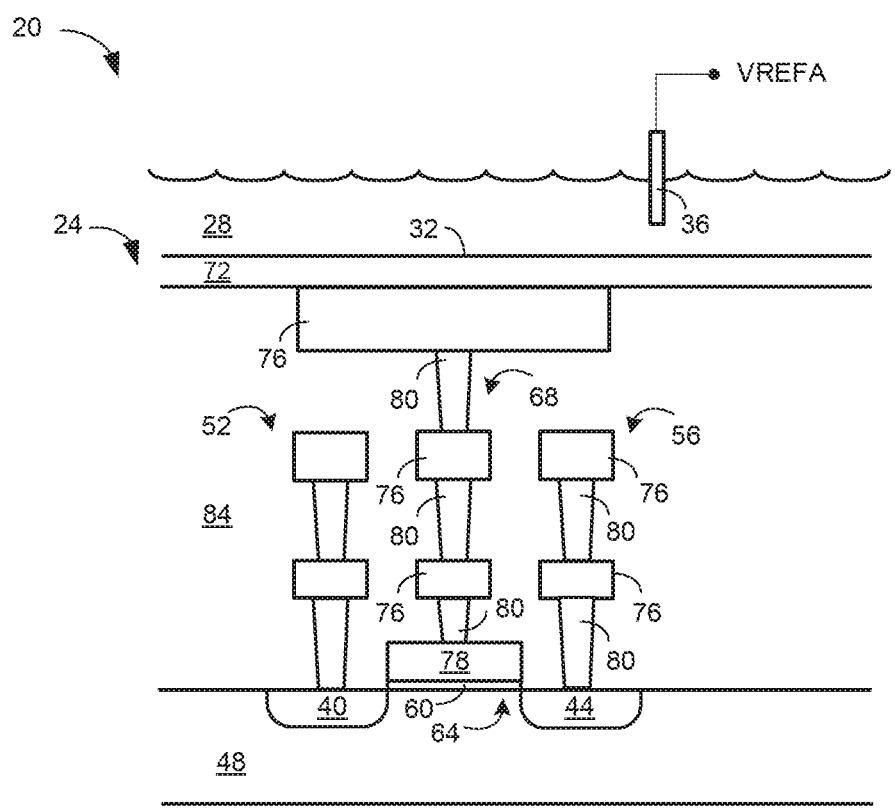
FIG. 1 is a cross-sectional diagram depicting an embodiment of an ion-sensing system including an ion-sensitive field effect transistor.

Providing a measure of the ion concentration in the form of an accumulated plurality of charge packets 216 can provide a measure having an increased signal level and signal-to-noise ratio, improved performance matching of a plurality of charge accumulation devices 104, and reduced flicker noise, in comparison to both providing a measure of the ion concentration in the form of only a single charge packet 216 and in the form of a threshold voltage variation, as discussed above in regard to FIG. 1. For example, due to the thermal activity of charges such as holes and electrons, generated charge packets are typically associated with a degree of noise. In one embodiment, the accumulation of a single charge packet may be accompanied by a noise charge error proportional to $k \cdot T \cdot C$, where k is Boltzmann's constant, T is the temperature in Kelvins, and C is the capacitance of the charge gathering region under the floating gate. When the charges are electrons, the voltage noise error for each collected packet can be equal to (square root of $(k \cdot T \cdot C))/q$, where q is the charge of an electron, and C is equal to the oxide capacitance Cox multiplied by the area of the floating gate 184. However, the signal-to-noise ratio SNR of an output signal based on the accumulation of a plurality of charge packets can be proportional to the square root of $(2 \cdot n \cdot C/k \cdot T)$, where n is the number of packets 216 accumulated, i.e., the number of operational cycles of the charge accumulation device 104 utilized to provide a single ion concentration measurement. Thus, the signal-to-noise ratio of the ion concentration measurement can increase in proportion to the square root of the number of packets 216 in a single measurement.

After accumulation at the drain 128 of the charge accumulation device 104, the plurality of charge packets 216 can be converted to an output signal or transferred out of the charge accumulation device using embodiments of the control and readout circuitry 112. The control and readout circuit 112 can control various aspects of both the cyclical operation of the charge accumulation device 104 and generation of an output signal based on the accumulated charge packets 216. The control and readout circuit 112 can control the charge accumulation device 104 by providing control signals to the source 124, drain 128, first control electrode 186 and second control electrode 188 to accumulate packets 216 at a selectable predetermined accumulation frequency. The accumulation frequency can be the frequency of operation of a single operational cycle of the charge accumulation device 104. The accumulation frequency can be selected based on or as a function of the anticipated rate of change of the ion concentration in the solution, the performance characteristics of the charge accumulation device 104 and control and readout circuitry 112, or a combination thereof. The control and readout circuit 112 can also control the generation of an output signal based on the charge packets 216 accumulated by the charge accumulation device 104 by providing control signals thereto to generate an output signal or transfer accumulated pluralities of charge packets 216 out of the charge accumulation device 104 at a selectable output generation frequency. The output generation frequency can be the frequency of generation of a single output signal value from the accumulated packets 216 in the charge accumulation device 104. The output generation frequency can be selected to be based on or be a function of the anticipated rate of change of the ion concentration in the solution 108, the performance characteristics of the charge accumulation device 104 and the control and readout circuitry 112, or a combination thereof. When the output signal is based on a plurality of accumulated charge packets 216, the output generation frequency can be less than the charge packet accumulation frequency.

Figure 5:
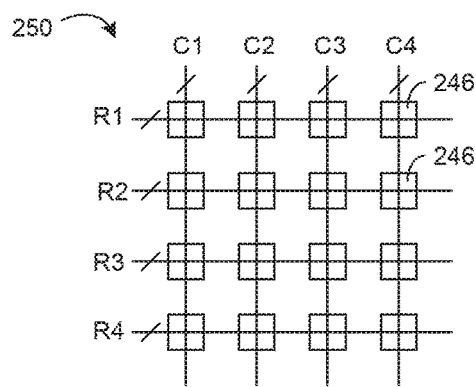
FIG. 5 is a schematic diagram depicting an embodiment of an ion-sensitive pixel array having a plurality of pixel circuits, each including the charge accumulation device and control and readout transistors.

A single charge accumulation device 104, along with associated portion of the control and readout circuitry 112 dedicated to that device 104, can represent a single ion-sensing pixel 246 in an array 250 of a plurality of ion-sensing pixels 246. FIG. 5 depicts an embodiment of an ion-sensing pixel array 250 having a plurality of ion-sensing pixels 246. Each pixel circuit 246 can include a charge accumulation device 104 and an associated portion of the control and readout circuit 112. The associated portion of the control and readout circuit 112 can be part of and dedicated to the particular pixel 246. The pixel array can be arranged into a plurality of rows and columns of pixels 246. The pixel array 250 can be controlled, addressed and have data input and output by a plurality of row and column control, addressing and data lines, including one or more row control, addressing and data lines R1-Rx, collectively referred to as row lines R1-Rx, and one or more column control, addressing and data lines C1-Cx, collectively referred to as column lines C1-Cx, for each row and each column.

Figure 6:
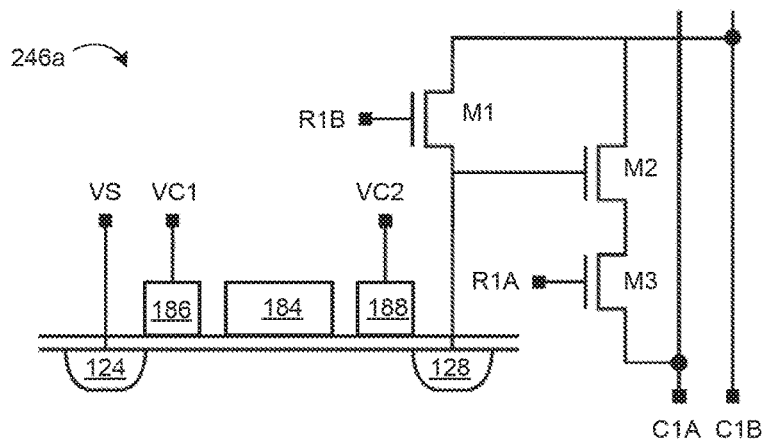
FIG. 6 is a partially cross-sectional, partially schematic diagram depicting an embodiment of a pixel circuit including the charge accumulation device and control and readout transistors.

FIG. 6 depicts an embodiment of an ion-sensing pixel 246a having embodiments of the charge accumulation device 104 and associated control and readout circuit portion 112. Note that FIG. 6 again depicts a simplified representation of the charge accumulation device 104, however embodiments of the depicted pixel 246a can include other components of the charge accumulation device 104, such as the additional components depicted in FIG. 2. The embodiment of FIG. 6 can be referred to as a three transistor, three electrode, or 3T3E, pixel 246. The control and readout circuit 112 can include three transistors, including a reset transistor M1 and a pair of readout transistors M2, M3. The charge accumulation device 104 can have three electrodes, including the first and second control electrodes 186, 188 and the floating gate 184. The control and readout circuit 112 can receive a plurality of column lines, including first and second column lines C1A, C1B, and a plurality of row lines, including first and second row lines R1A, R1B.

For purposes of discussion with reference to sources and drains, etc., it will be assumed that the control and readout transistors M1, M2, M3 in the pixel embodiment 246a of FIG. 6, and in other pixel embodiment depictions discussed herein, are NMOS transistors. However, in other pixel embodiments, the control and readout transistors can be either NMOS or PMOS transistors, or any combination thereof. In FIG. 6, the first readout transistor M2 can have a gate connected to the drain region 128 of the charge accumulation device 104, a source connected to a drain of the second readout transistor M3, and a drain connected to the second column line C1B. The second readout transistor M3 can have a gate connected to the first row line R1A, a source connected to the first column line C1A, and a drain connected to the source of the first readout transistor M2. The reset transistor M1 can have a source connected to the drain 128 of the charge accumulation device 104, a gate connected to the second row line R1B, and a drain connected to the second column line C1B.

The embodiment of the control and readout circuit 112 of FIG. 6 can be used to control the charge accumulation device 104 and generate an output signal in conjunction with the operation of the charge accumulation device 104 depicted in FIGS. 3A-3D and FIG. 4. In a reset operation, the reset transistor M1 and the second row and column lines R1B, C1B can be used to reset the charge accumulation device 104 in the pre-cycle reset phase, as discussed above. For example, a logic high signal, or high-valued voltage such as an upper power supply, can be delivered to the second row and column lines R1B, C1B while a logic low signal, or low-valued voltage such as a low power supply, can be delivered to the first row line R1A, to turn on the rest transistor M1 while turning off the second readout transistor M3. This can deliver a high voltage value to the drain region 128 of the charge accumulation device 104, resulting in the clearing out of any charge packets 216 accumulated at the drain 128, thus resetting the charge accumulation device 104.

In a readout operation, the readout transistors M2, M3 and the first row and column lines R1A, C1A can be used to generate an output signal as a function of the charge packets 216 accumulated at the drain region 128 of the charge accumulation device 104 after one or more cycles of operation of the device 104, as discussed above. For example, a logic high signal or high-valued voltage such as an upper power supply, or alternatively an intermediate-valued voltage such as a voltage between the upper and lower power supplies, can be delivered to the first row line R1A while a logic low signal, or low-valued voltage such as a low power supply, can be delivered to the second row line R1B, essentially activating the first and second readout transistors M2, M3 while turning off the reset transistor M1. In this mode, the first and second readout transistors M2, M3 can act as an amplifier to convert the one or more charge packets 216 accumulated at the drain region 128 of the charge accumulation device 104 to a voltage output signal on the first column line C1A. The first readout transistor M2 can be modeled as operating in a source follower configuration, receiving an input voltage from the drain 128 of the charge accumulation device 104 and providing an intermediate output voltage at its source to the drain of the second readout transistor M3. The conversion of the charge packets 216 to an input voltage at the drain 128 of the charge accumulation device 104 can be an inherent result of the accumulation of charge at the drain 128. The second readout transistor M3 can be modeled as operating in a cascode configuration with respect to the source follower first readout transistor configuration, thereby boosting the gain of the two transistor combination in comparison to the source follower alone. The second readout transistor M3 can receive the intermediate output from the source of the source follower and provide the output voltage to the first column line C1A at this source.

Figure 7:
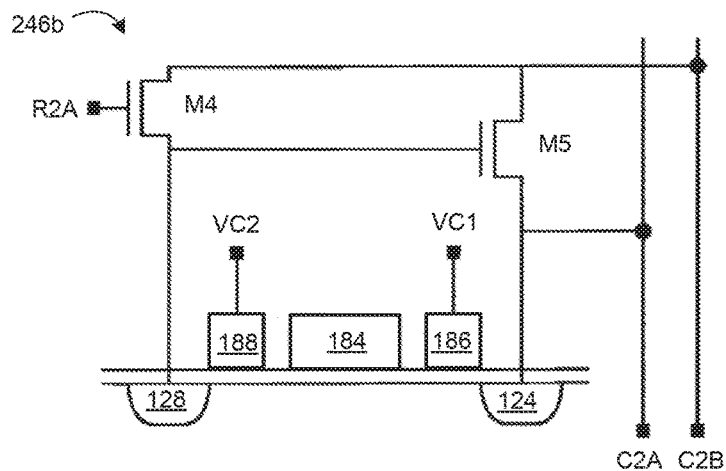
FIG. 7 is a partially cross-sectional, partially schematic diagram depicting another embodiment of a pixel circuit including the charge accumulation device and control and readout transistors.

FIG. 7 depicts another embodiment of an ion-sensing pixel 246b having embodiments of the charge accumulation device 104 and associated control and readout circuit portion 112. Note that FIG. 7 again depicts a simplified representation of the charge accumulation device 104, however embodiments of the depicted pixel 246b can include other components of the charge accumulation device 104, such as the additional components depicted in FIG. 2. The embodiment of FIG. 7 can be referred to as a two transistor, three electrode, or 2T3E, pixel. The control and readout circuit 112 can include two transistors, including a reset transistor M4 and a readout transistor M5, and the charge accumulation device 104 can have three electrodes, including the first and second control electrodes 186, 188 and the floating gate 184. The control and readout circuit 112 can receive a row line R2A and a plurality of column lines, including first and second column lines C2A, C2B.

The pixel embodiment 246b of FIG. 7 can reduce the number of readout transistors, in comparison to the pixel embodiment 246a of FIG. 6, by management of the voltage at the drain 128 of the charge accumulation device 104 to eliminate the need for a row select functionality served by the first row line R1A of the pixel embodiment 246a of FIG. 6. The drain 128 in each of FIGS. 7 and 9, also called a floating diffusion 128, can have the property of a capacitance. The row select device can be eliminated by managing the floating diffusion potential when the pixel 246b is not active. The gate tied to the floating diffusion 128, for example M5 in FIG. 7, can remain at a low potential in order to disable the source follower M5 when not in use. Therefore, after the pixel 246b has been read out, the floating diffusion 128 can be sampled to a low potential and then left at that potential until the pixel 246b is read again. A reason the potential stays low can be that the floating diffusion 128 acts like a capacitor that holds the low voltage sampled onto it.

In FIG. 7, note that the depicted spatial arrangement of the first and second control electrodes 186, 188 is reversed from that shown in previous figures, with the first control electrode 186 depicted on the right-hand side and the second control electrode 188 depicted on the left-hand side. Again, for purposes of discussion with reference to sources and drains, etc., it will be assumed that the control and readout transistors are NMOS transistors, however the control and readout transistors in any of the pixel embodiments can be either NMOS or PMOS transistors, or any combination thereof. The reset transistor M4 can have a source connected to the drain 128 of the charge accumulation device 104, a gate connected to the row line R2A, and a drain connected to the second column line C2B. The readout transistor M5 can have a gate connected to the drain region 128 of the charge accumulation device 104 (and thus also the source of the reset transistor M4), a source connected to the source 124 of the charge accumulation device 104 and the first column line C2A, and a drain connected to the second column line C2B.

FIGS. 8A-8D depict an embodiment of the operation of the pixel embodiment 246b of FIG. 7 to accumulate a plurality of charge packets 216 as a function of the solution ion concentration and generate an output signal as a function of the accumulated charge packets 216. FIGS. 8A-8D depict a plurality of complete cycles of an embodiment of operation of the charge accumulation device 104. Similarly to FIGS. 3A-3D, the top of each of FIGS. 8A-8D depicts a simplified partially cross-sectional, partially schematic representation of the pixel 246, including the charge-accumulation device 104 and control and readout transistors M4, M5. For convenience of illustration and explanation, other components of the charge-accumulation device 104 and control and readout transistors M4, M5 are omitted from the depictions, although omitted components can be present in actual embodiments. In each figure, below the representation of the charge-accumulation device 104 and control and readout transistors M4, M5 are four diagrams depicting, in a manner spatially aligned to the pixel representation above, potential energies and charge accumulation in the charge accumulation device 104 and control and readout transistors M4, M5 at different phases of an operational cycle of the pixel 246b.

In a reset phase 254, the reset transistor M4 and the row and second column line R2A, C2B can be used to reset the charge accumulation device 104. A logic high signal, or high-valued voltage such as an upper power supply, can be delivered to the row and second column lines R2A to turn on both the rest transistor M4 and the readout transistor M5. This can deliver a high voltage value to both the drain 128 and source 124 of the charge accumulation device 104, resulting in the clearing of any charge accumulated at the drain and source 128, 124 of the charge accumulation device 104, and thus resetting the device 104.

In a first phase 258 of the operational cycle, the reset transistor M4 can be turned off and a potential barrier raised (i.e., a low potential created) under the second electrode 188, preparing the charge accumulation device 104 for generating a charge packet 216 under the floating gate 184. The reset transistor M4 can be turned off and the low potential under the second electrode 188 created by delivering a logic low or low-valued voltage to the row line R2A and second control electrode 188. Note that at the end of the first phase 258, a high potential, and thus a low potential barrier, is left existing under the gate of the readout transistor M4.

In a second stage 262 of the operational cycle, charge, e.g., electrons, can be injected into the p-type region 224 under the floating gate 184 from the n-type source region 124 of the charge-accumulation device 104. The charge 264 can flood the charge accumulation device 104 from the source 124 to under the floating gate 184, but not under the second control electrode 188. Charge can be injected into the charge accumulation device 104 through the source 124 in various ways, such as through the use of a current source or charge pump selectively injecting charge into the source 124, or by applying a suitable voltage to the source 124 in the context of voltages supplied to or manifesting on the first control electrode 186 and floating gate 184, such as, e.g., a logic-low or low-valued voltage. The charge can be injected under the floating gate 184 through the source 124 using the first column line C2A, and thus charge 265 can simultaneously be injected into the readout transistor M4, including both its source and drain regions and under its gate, due to the low potential barrier left existing under the gate of this transistor M4 after the first phase 258 of the operational cycle.

In a third stage 266, the charge injection into the charge accumulation device and readout transistor can be ended, and excess charge in these devices withdrawn. However, because a potential differential can exist between under the first control electrode 186 and under the floating gate 184, a charge packet 216 can remain under the floating gate 184 as a function of this potential difference. As discussed above in regard to FIGS. 3A-3D, the size of the charge packet 216 remaining under the floating gate 184 in this stage 266 can be a function of the voltage applied to the first control electrode 186 and the voltage manifesting on the floating gate 184 due to the ion concentration in the solution 108, and thus be a measure of the ion concentration in the solution 108, given a known voltage applied to the first control electrode 186.

Figures 8A, 8B, 8C, 8D:
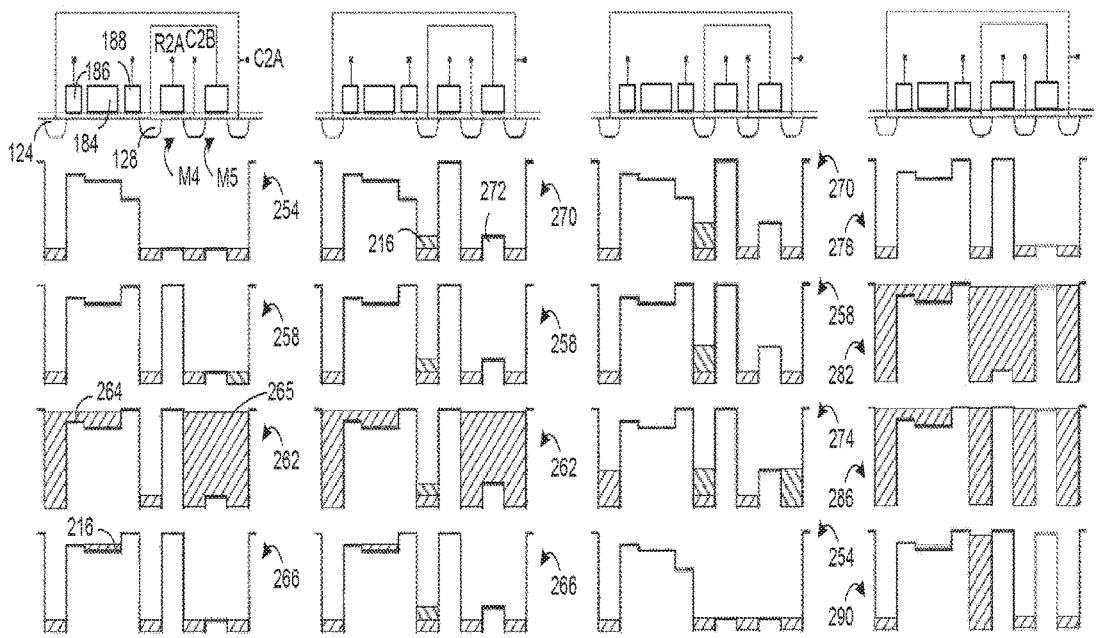
FIGS. 8A-8D are cross-sectional, potential and charge diagrams depicting embodiments of operation of the pixel circuit depicted in FIG. 7.

Finally, in a last phase 270 of the first operational cycle, depicted in FIG. 8B, the charge packet 216 remaining under the floating gate 184 after the third stage 266 of the cycle can be transferred from under the gate 184, through the region 232 under the second control electrode 188, and into the drain diffusion region 128, where it can be maintained, similar to as discussed above in regard to the first phase 220 of the operational cycle of FIGS. 3A-3D. The charge packet 216 can be transferred to the drain region 128 by lowering the potential barrier under the second control electrode 188 by delivering a logic high or high-valued voltage to the second control electrode 188. The charge delivered to the drain 128 of the charge accumulation device 104 incrementally decreases the voltage at this drain 128, and because the gate of the readout transistor M5 is connected to the drain 128, the charge packet 216 thus also incrementally increases the voltage at the gate of the readout transistor M5, as evidenced by the incrementally decreased potential barrier 272 under the gate of this readout transistor M5 at the end of the last stage 270 of the operational cycle. In this way, the voltage at and the potential under the gate of the readout transistor M5 can be a function of the charge packets 216 accumulated at the drain 128 of the charge accumulation device 104 at the end of every operational cycle.

FIGS. 8B-8C depict a second operational cycle, in which another charge packet is accumulated as in the first operational cycle depicted in FIGS. 8A-8B, with the result being the voltage at and the potential under the gate of the readout transistor again tracking the size of the plurality of accumulated charge packets 216. FIG. 8C also depicts another reset phase after the second operational cycle.

An output can be generated by sampling the voltage at the source of the readout transistor M5. This can occur during a readout phase 274. The output can also be generated using a double sampling technique in which both a first output and a second output is provided. The first output can represent an output produced by a background level of charge present at the drain 128 of the charge accumulation device 104. The second output can represent an output produced by a both the background level of charge and the plurality of charge packets 216 accumulated at the drain 128. Subtracting the first output from the second output can thus produce a more accurate measurement of the charge packets 216 accumulated to represent the ion concentration of the solution 108. In one embodiment, the first output can be sampled during the first phase 258 of the operational cycle. The second the second output can then be that sampled during the readout phase 274.

FIG. 8D also depicts an embodiment of a deactivation sequence for a row of the pixels of the embodiment 246a depicted in FIG. 7. In a first phase 278 of the deactivation sequence, a logic low or low-valued voltage is delivered to the row line R2A, while a logic high or high valued voltage is delivered to the first column line C2A. In a second phase 282 of the deactivation sequence, a logic high or high-valued voltage is delivered to the row line R2A, while the a logic low or low valued voltage is delivered to the first column line C2A. In a third phase 286 of the deactivation sequence, a logic low or low-valued voltage is delivered to the row line R2A, while the logic low or low valued voltage is maintained at the first column line C2A. In a fourth phase 290 of the deactivation sequence, a logic low or low-valued voltage is maintained on the row line R2A, while a logic high or high valued voltage is delivered to the first column line C2A.

Figure 9:
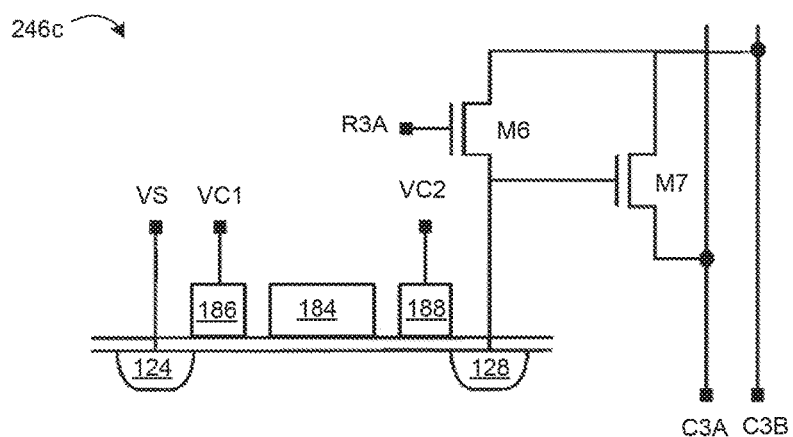
FIG. 9 is a partially cross-sectional, partially schematic diagram depicting another embodiment of a pixel circuit including the charge accumulation device and control and readout transistors.

FIG. 9 depicts another embodiment 246c of a two transistor, three electrode, or 2T3E, pixel. The control and readout circuit 112 can include two transistors, including a reset transistor M6 and a readout transistor M7, and the charge accumulation device 104 can have three electrodes, including the first and second control electrodes 186, 188 and the floating gate 184. The control and readout circuit 112 can receive a row line R3A and a plurality of column lines, including first and second column lines C3A, C3B. The reset transistor M6 can have a source connected to the drain 128 of the charge accumulation device 104, a gate connected to the row line R3A, and a drain connected to the second column line C3B. The readout transistor M7 can have a gate connected to the drain region 128 of the charge accumulation device 104 (and thus also the source of the reset transistor M6), a source connected to first column line C3A, and a drain connected to the second column line C3B. Turning on the reset transistor M6 can remove the charge packets 216 accumulated at the drain 128 of, and thus reset, the charge accumulation device 104, similarly to as discussed with respect to various embodiments above. With the reset transistor M6 turned off, the readout transistor M7 can provide an output voltage as a function of the charge packets 216 accumulated at the drain 128 of the charge accumulation device 104 operating in a source follower configuration, or provide an output current as a function of the charge packets 216 accumulated at the drain 128 of the charge accumulation device 104 operating in a common source configuration.

Figure 10:
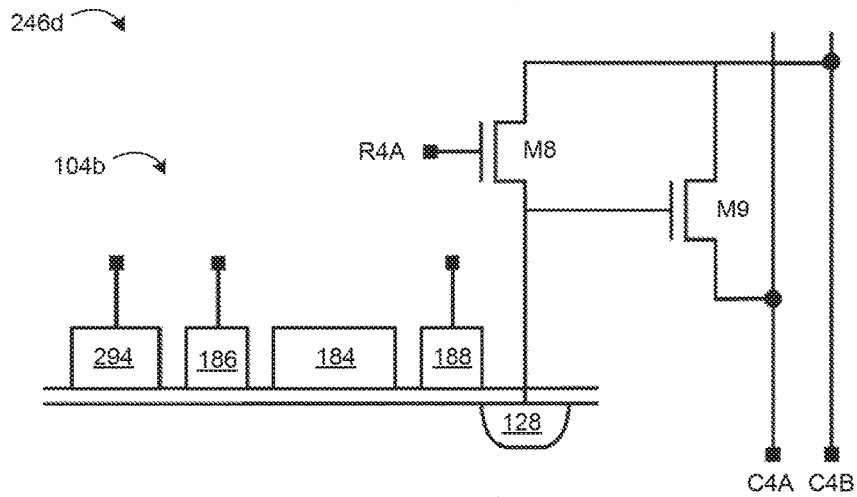
FIG. 10 is a partially cross-sectional, partially schematic diagram depicting another embodiment of a pixel circuit including the charge accumulation device and control and readout transistors.

The charge accumulation device 104 can also include more than two control electrodes. FIG. 10 depicts an embodiment of an ion-sensing pixel 246d having two control and readout transistors and four charge accumulation device electrodes, including three control electrodes and a floating gate. Although FIG. 10 depicts a simplified representation of the charge accumulation device 104b, actual embodiments can include other components of the charge accumulation device, such as components depicted in FIG. 2. The electrodes of the charge accumulation device 104b can include a first and second electrode 186, 294 on one side of the floating gate 184 and a third electrode 188 on the other side of the floating gate 184. The charge accumulation device 104*b* of FIG. 10 may not include a source region, but can include a drain region 128 adjacent to the region under the third electrode 188. The control and readout circuit 112 is the same as that depicted in FIG. 9, and can include two transistors, including a reset transistor M8 and a readout transistor M9, and receive a row line R4A and a plurality of column lines, including first and second column lines C4A, C4B. The reset transistor M8 can have a source connected to the drain 128 of the charge accumulation device 104*b*, a gate connected to the row line R4A, and a drain connected to the second column line C4B. The readout transistor M9 can have a gate connected to the drain region 128 of the charge accumulation device 104*b* (and thus also the source of the reset transistor M8), a source connected to first column line C4A, and a drain connected to the second column line C4B. The reset and readout transistors M8, M9 can operate as they can in the embodiment of FIG. 9.

FIGS. 11A-11D depict an embodiment of the operation of the pixel embodiment 246*d* of FIG. 10 to accumulate a plurality of charge packets 216 as a function of the solution ion concentration and generate an output signal as a function of the accumulated charge packets 216. FIGS. 11A-11D depict a plurality of complete cycles of an embodiment of operation of the charge accumulation device 104*b*. The top of each of FIGS. 11A-11D depicts a simplified partially cross-sectional, partially schematic representation of the charge-accumulation device 104*b* and control and readout transistors M8, M9 of FIG. 10. For convenience of illustration and explanation, other components of the charge-accumulation device 104*b* and control and readout transistors M8, M9 are omitted from the depictions, although omitted components can be present in actual embodiments. In each figure, below the representation of the charge-accumulation device 104*b* and control and readout transistors M8, M9 are four diagrams depicting, in a manner spatially aligned to the pixel representation above, potential energies and charge accumulation in the charge accumulation device 104*b* and control and readout transistors M8, M9 at different phases during the operational cycle of the pixel 246*d*.

Figures 11A, 11B, 11C, 11D:
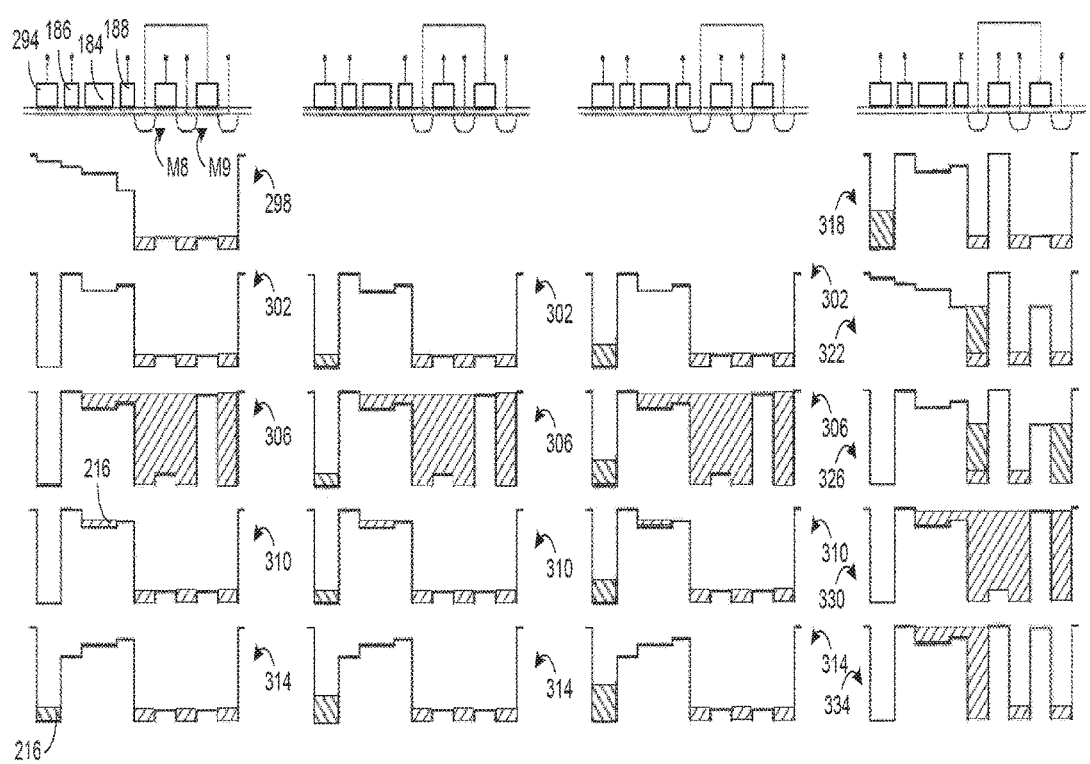
FIGS. 11A-11D are cross-sectional, potential and charge diagrams depicting embodiments of operation of the pixel circuit depicted in FIG. 10.

In a reset phase 298 depicted in FIG. 11A, a potential gradient can be created from left to right under the first electrode 294, second electrode 186, floating gate 184 and third electrode 188, and a logic high or high-voltage value delivered to the gate of the reset transistor M8 to clear any charge from the charge accumulation device 104*b* remaining from previous operations.

In a first phase 302 of an operational cycle of the pixel 246*d*, the potential barrier under the third electrode 188 can then be raised higher than that in the reset phase 298 and that that existing on the floating gate 184. In a second phase 306 of the pixel operational cycle, charge can be injected into the charge accumulation device 104*b* through the drain diffusion node 128. In a third phase 310, the injected charge can be withdrawn from the charge accumulation device 104*b*, while a charge packet 216 remains under the floating gate 184 due to the potential barrier differential between the floating gate 184 and the third electrode 188 established in the second phase 306. In a fourth and final phase 314 of the operational cycle, a potential gradient can be created from right to left under the third electrode 188, floating gate 184, second electrode 186 and first electrode 186, to move the charge packet 216 from under the floating gate 184 to under the first electrode 294.

This accumulation cycle can then be repeated a plurality of times, as depicted in FIGS. 11B-11C, to accumulate a plurality of charge packets 216 under the first electrode 294.

FIG. 11D depicts a readout sequence to generate an output a signal based on the size of the plurality charge packets 216 accumulated under the first electrode 294. The readout sequence can incorporate a double sampling technique in which both a first output and a second output is provided. The first output can represent an output produced by a background level of charge present at the drain 128 of the charge accumulation device 104*b*. The second output can represent an output produced by a both the background level of charge and the plurality of charge packets 216 accumulated at the first electrode 294 after they have been transferred to the drain 128 of the charge accumulation device 104*b*. Subtracting the first output from the second output can thus produce a more accurate measurement of the charge packets 216 representing the measurement of the solution ion concentration. In a first phase 318 of the readout sequence, the first output can be provided by the readout transistor M9 while the plurality of charge packets 216 are still accumulated under the first electrode 294. In a second phase 322 of the readout sequence, a potential gradient can be created from left to right under the first electrode 294, second electrode 186, floating gate 184 and third electrode 188 to move the plurality of charge packets 216 from under the first electrode 294 to the drain 128 of the charge accumulation device 104*b*. After the second phase 322, in a third phase 326 of the readout sequence, the second output can be provided by the readout transistor M8.

FIG. 11D also depicts two phases 330, 334 of a deactivation sequence for a row of the pixel embodiments 246*d* of FIG. 10.

Variations on the above discussed embodiments are possible. Although embodiments of the charge accumulation device have been depicted and discussed herein as including n-type sources and drains, and p-type regions under the floating gate and control electrodes, in embodiments this relationship can also be reversed, with the charge accumulation device including p-type sources and drains, and n-type regions under the gate and control electrodes. Although FIG. 2 depicts an epitaxial p-type region under the control electrodes an floating gate, in embodiments a p-type or n-type region under the control electrodes and floating gate can include a diffusion region or other type of p-type or n-type region instead of or in addition to an epitaxial region. Although various control and readout transistors have been discussed herein as including NMOS transistors, in embodiments the control and readout transistors can include NMOS transistors, PMOS transistors, or any combination thereof. In some embodiments, rows and columns of pixels of the pixel array can share some or all of the row and column lines. Although in some embodiments discussed herein, charge carriers and charge packets have been assumed to be electrons, in other embodiments charge carriers and charge packets can comprise holes. Although stages of operational cycles of the charge accumulation device have been discussed herein as occurring in certain orders, and having certain labels (e.g., first phase, second phase, etc.), in other embodiments, the labels and stages of the operational cycles can be changed, rearranged, added to, subtracted to, etc. Although embodiments of the charge accumulation device have been discussed as having two or three control electrodes, in other embodiments, the charge accumulation device can have more or less than two or three control electrodes. Although certain embodiments of control signals have been depicted and discussed herein, in other embodiments, the various control signals can take different forms.

Additional embodiments of the charge accumulation device 104 and ion sensitive pixel 246 are also possible. For example, any feature of any of the embodiments of the charge accumulation device 104 and ion sensitive pixel 246 described herein can optionally be used in any other embodiment of the charge accumulation device 104 and ion sensitive pixel 246. Embodiments of the charge accumulation device 104 and ion sensitive pixel 246 can also optionally include any subset of the components or features of any embodiments of the charge accumulation device 104 and ion sensitive pixel 246 described herein.

Although the invention has been described above with reference to specific embodiments, the invention is not limited to the above embodiments and the specific configurations shown in the drawings. The operation processes are also not limited to those shown in the examples. Those skilled in the art will appreciate that the invention may be implemented in other ways without departing from the sprit and substantive features of the invention. The present embodiments are therefore to be considered in all respects as illustrative and not restrictive. The scope of the invention is indicated by the appended claims rather than by the foregoing description, and all changes that come within the meaning and range of equivalency of the claims are therefore intended to be embraced therein.

Several embodiments of the present invention are specifically illustrated and described herein. However, it will be appreciated that modifications and variations of the present invention are covered by the above teachings. In other instances, well-known operations, components and circuits have not been described in detail so as not to obscure the embodiments. It can be appreciated that the specific structural and functional details disclosed herein may be representative and do not necessarily limit the scope of the embodiments.

Those skilled in the art may appreciate from the foregoing description that the present invention may be implemented in a variety of forms, and that the various embodiments may be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and following claims.

Various embodiments may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

Some embodiments may be implemented, for example, using a computer-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disc Read Only Memory (CD-ROM), Compact Disc Recordable (CD-R), Compact Disc Rewriteable (CD-RW), optical disk, magnetic media, magneto-optical media, removable memory cards or disks, various types of Digital Versatile Disc (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

What is claimed:

1. A method of detecting an ion concentration of a fluid, comprising:
   passing the fluid over an ion-sensitive passivation surface above an electrically floating gate structure of a charge accumulation device of an ion sensitive circuit, wherein the floating gate includes a plurality of conductors electrically coupled to one another and separated by dielectric layers;
   applying a control signal to a first charge control electrode disposed on a gate oxide layer and formed over a first electrode semiconductor region of the charge accumulation device to control entry of charge from the ion concentration of the fluid to form a packet of charge in a gate semiconductor region below the electrically floating gate structure;
   applying a control signal to a second charge control electrode disposed on the gate oxide layer and formed over a second electrode semiconductor region of the charge accumulation device to control transmission of the charge packet out of the gate semiconductor region and into a drain diffusion region;
   accumulating a plurality of charge packets at the drain diffusion region of the charge accumulation device as a function of the ion concentration in the fluid at a selectable charge packet accumulation frequency; and
   generating an output signal using at least one control and readout transistor as a function of the accumulated plurality of charge packets at the drain diffusion region at a selectable output signal generation frequency, wherein the output signal represents a measure of the ion concentration in the fluid.

2. The method of claim 1, further comprising individually transmitting, one at a time, the plurality of charge packets through the second electrode semiconductor region in response to the applying the control signal to the second charge control electrode.

3. The method of claim 1, further comprising removing any charge packets previously accumulated at the drain diffusion region prior to accumulating the plurality of charge packets.

4. The method of claim 1, wherein the output signal generation frequency is less than the charge packet accumulation frequency.

* * * * *